United States Patent [19]

Roy et al.

[11] Patent Number: 5,556,956

[45] Date of Patent: Sep. 17, 1996

[54] METHODS AND COMPOSITIONS RELATING TO THE ANDROGEN RECEPTOR GENE AND USES THEREOF

[75] Inventors: Arun K. Roy; Bandana Chatterjee, both of San Antonio, Tex.

[73] Assignee: Board of Regents, The University of Texas System, Austin, Tex.

[21] Appl. No.: 149,096

[22] Filed: Nov. 4, 1993

[51] Int. Cl.$^6$ .......................... C07H 21/00; C07H 21/02; C07H 21/04

[52] U.S. Cl. .................... 536/24.1; 536/24.3; 536/24.31; 536/23.1

[58] Field of Search .............................. 536/24.1, 24.31, 536/24.3, 23.1; 514/44

[56] References Cited

PUBLICATIONS

Mackellar et al. (1992) Nucleic Acids Res. 20(13), 3411–3417.
Milligan et al. (1993) J Med. Chem. 36(14), 1923–1937.
Uhlmann et al. (1990) Chem. Rev. 90(4), 543–584.
Wasylyk (1988) Biochem Biophys Acta 951, 17–35.
Xodo et al. (1991) Nucleic. Acids Res. 19(20), 5625–5631.
Agrawal, Sudhir, et al. "Cellular Uptake and Anti–HIV Activity of Oligonucleotides and Their Analogs", *Gene Regulation: Biology of Antisenses RNA and DNA*, 2737–283, 1992.
Agrawal, Sudhir and J.–Y. Tang, "Efficient Synthesis of Oligoribonucleotide and its Phosphorothioate Analogue Using H–Phosphonate Approach", *Tetrahedron Letters*, 31(52):7541–7544, 1990.
Akhtar, Saghir, et al., "Pharmaceutical Aspects of the Biological Stability and Membrane Transport Characteristics of Antisense Oligonucleotides", *Gene Regulation: Biology of Antisense RNA and DNA*, 133–145, 1992.
Baarends, Willy M., et al., "The rat androgen receptor gene promoter", *Molecular and Cellular Endocrinology*, 74:75–84, 1990.
Bankier, A. T., et al., "Random cloning and sequencing by the M13/dideoxynucleotide chaim termination method", *Methods Enzymol*, 155:51–93, 1987.
Beato, M., "Gene regulation by steroid hormones" *Cell*, 56(3): 335–44, 1989.
Biggin, M.D. and Tjian, R., "Transcription factors and the control of Drosophila development", *Trends in Gent*, 5(11):377–83.
Biro, Sadatoshi, et al., "Inhibitory effects of antisense oligodeoxynucleotides targeting c–myc mRNA on smooth muscle cell proliferation and migration", *Proc. Natl. Acad. Sci. USA*, 90:654–658, 1993.
Boutorin, A.S., et al., "Synthesis of alkylating oligonucleotide derivatives containing cholesterol or phenazinium residues at their 3'–terminus and their interaction with DNA within mammalian cells", *Institute of Biorganic Chemistry, Siberian Division of the USSR Academy of Sciences*, 254(1, 2):129–132, 1989.
"Antisense Therapeutics", *Gene Regulation: Biology of Antisense RNA and DNA*, 285–293, 1992.

Briggs, M. R., et al., "Purification and Biochemical Characterization of the Promoter–Specific Transcription Factor", *Science*, 234:47–52, 1986.
Carthew, R. W., et al., "An RNA polymerase II transcription factor binds to an upstream element in the adenovirus major late promoter", *Cell*, 43(2 Pt 1):439–48, 1985.
Chang, R. W., et al., "Molecular cloning of human and rat complementary DNA encoding androgen receptors", *Science*, 240:324–26, (1988).
Christy, B. and Nathans, "DNA binding site of the growth factor–inducible protein zif268", *Proc Natl Acad Sci U S A* 86(22):8737–41, 1989.
Cohen, Jack S., "Chemically modified oligodeoxynucleotide analogs as regulators of viral and cellular gene expression", *Gene Regulation: biology of Antisense RNA and DNA*, 247–259, 1992.
Coffey, D. S. and Pienta, K. J., "New Concepts in Stydying the Control of Normal and Cancer Growth of the Prostate", *Prog. Clin. Biol. Res.*, 239:1–73, (1987).
Colvard, D. S., et al., "Identification of Androgen Receptors in Normal Human Osteoblast–like Cells", *Proc. Natl. Acad. Sci U S A* 86(3):854–7, (1989).
Curran, T. and Franza, B. R., Jr., "Fos and Jun: the AP–1 Connection", *Cell*, 55(3):395–7, (1988).

(List continued on next page.)

Primary Examiner—Mindy Fleisher
Assistant Examiner—David Schmickel
Attorney, Agent, or Firm—Akin, Gump, Strauss, Hauer & Feld, L.L.P.

[57] ABSTRACT

Disclosed are methods and compositions, including antisense and antigene constructs and pharmaceutical formulations thereof, for use in regulating androgen receptor gene expression. The promoter activity of the androgen receptor gene is herein shown to include a critical upstream acting domain with a unique sequence, the unique nucleic acid sequence corresponding to positions 1697 and 2084, particularly between positions 1697 and 1717, as defined in SEQ ID NO:1. The AR gene promoter sequence, herein characterized as having a a particular nucleotide sequence defined between nucleotides 1697 and 2084 of SEQ ID NO:1, is characterized as important in the regulation of androgen receptor gene expression. Oligonucleotides and triple helix forming oligonucleotides (TFO) that bind to this region and that have nucleic acid sequences corresponding particularly to the region between positions 1697 and 2084 of the androgen receptor gene promoter region provide specific and potent inhibition of AR promoter region function in cellulo. Rat and human nuclear proteins, more specifically described as novel trans-activating proteins that specifically bind to this region of the androgen receptor gene, are also identified. These proteins may be used to prepare specific antibodies to the protein, as well as to regulate the expression of the AR gene. The oligonucleotide compositions of the invention may be used as molecular probes for the androgen receptor gene, as well as to inhibit the expression of the androgen receptor gene. The compositions may also be used in the treatment of pathologies characterized by overexpression of the androgen receptor gene, including prostatic hypertrophy and androgenetic alopecia.

15 Claims, 5 Drawing Sheets

PUBLICATIONS deWet, "Firefly Luciferase Gene: Structure and Expression in Mammalian Cells", *Mol Cel Biol,* 2:1044–51, 1987.

Encio, I. J. and Detera–Wadleight, S. D. "The genomic structure of the human glucocorticoid receptor", *J Biol CHem,* 266:7182–88, 1991.

Evans, R. M., "The steroid and thyroid hormone receptor superfamily", *Science,* 240(4854):889–95, 1988.

Faber, P. W., et al., "Characterization of the human androgen receptor transcription unit", *J Biol Chem,* 266(17):10743–49, 1991.

Hall, C. V., et al., "Expression and Regulation of *Escherichia coli* lacZ gene gusions in mammalian cells", *J Mol Appl Genet,* 2:101–0, 1983.

Hanvey, Jeffery C., et al., "Antisense and Antigene Properties of Peptide Nucleic Acids", *Science,* 258:1481–1485, 1992.

Harris, Georgianna, et al., "Indentification and selective inhibition of an isozyme of steroid 5a–reductase in human scalp", *Proc. Natl. Acad. Sci. USA,* 89:10787–10791, 1992.

Huckaby, C. S., et al., "Structure of the chromosomal chicken progesterone receptor gene", *Proc Natl Acad Sci U S A* 84(23):8380–4.

Issemann, I. and Green, S., "Activation of a member of the steroid hormone receptor superfamily by peroxisome proliferactors", *Nature,* 347:645–50, 1990.

Jenster, G., et al., "Functional domains of the human androgen receptor", *J Steroid Biochem Mol Biol,* 41(3–8):671–75, 1992.

Klemsz, M. J., et al., "The macrophage and B cell–specific transcription factor PU.1 is related to the ets oncogene", *Cell,* 61:113–24, 1990.

Krieg, Arthur M., et al., "Modification of antisense phosphodiester oligodeoxynucleotides by a 5' cholesteryl moiety increases cellular association and improves efficacy", *Proc. Natl. Acad. Sci. USA,* 90:1048–1052, 1993.

Leclerc, S., et al., "Purification of a human glucocorticoid receptor gene promoter–binding protein", *J Biol Chem,* 266(14):8711–19, 1991.

Leiter, Josef M., et al., "Inhibition of influenza virus replication by phosphorothioate oligodeoxynucleotides", *Proc. Natl. Acad. Sci. USA,* 87:3430–3434, 1990.

Lubahn, D. B., et al., "Cloning of human androgen receptor complementary DNA and localizing to the X chromosone", *Science, 240(4850):327–30, 1988.*

Marcelli, M., et al., "Androgen resistance associated with a mutation of the androgen receptor at amino acid levels and impairment of receptor function", *J Clin Endocrinol Metab,* 73(2):318–25, 1991.

Marshall, W. S. and M. H. Caruthers, "Phosphorodithioate DNA as a Potential Therapeutic Drug", *Science,* 259:1564–1570, 1993.

Martin, M. E., et al., "Activation of the polyomavirus enhancer by a murine activator protein 1 (AP1) homolog and two contiguous proteins", *Proc Natl Acad Sci U S A,* 85:5839–43, 1988.

McEwen, B. S., "Binding and metabolism of sex steroids by the hypothalamic–pituitary unit: physiological implications", *Annu Rev Physiol,* 42:97–110, 1980.

Milin, B. and Roy, A. K., "Androgen receptor in rat liver: Cytosol receptor deficiency in the pseudohermaphrodite male rate", *Nature: New Biol,* 242:248–50, 1973.

Newmark, J. R., et al., "Androgen receptor gene mutations in human prostate cancer", *Proc Natl Acad Sci U S A,* 89:6319–23, 1992.

Oberhauser, Berndt and Ernest Wagner, "Effective incorporation of 2' –O–methyl–oligoribonucleotides into liposomes and enhanced cell association through modification with thiocholesterol", *Nucleic Acids Research,* 20(3):533–538, 1992.

O'Malley, B., "The steriod receptor superfamily: More excitement predicted for the future", *Mol Endocrinol,* 4:363–69, 1990.

Pajunen, A. E. I., et al., "Androgenic regulation of ornithine decarboxylase activity in mouse kidney and its relationship to changes in cytosol and nuclear androgen receptor concentrations", *J Biol Chem,* 257(14):8190–98, 1982.

Pinsky, L. and Kaufman, M., "Genetics of steroid receptors and their disorders", *Adv Hum Genet,* 16;299–472, 1987.

Roberts, Richard W. and Donald M. Crothers, "Stability and Properties of Double and Triple Helices: Dramatic Effects of RNA or DNA Backbone Composition", *Science, 258:1463–1466, 1992.*

Ron, D., et al, "An inducible 50 kilodalton NFkB–like protein and a constitutive protein both bind the acute–phase response element of the angiotensinogen gene", *Mol Cell Biol,* 10:1023–32, 1990.

Saunders, P. T. K., et al., "Point mutations detected in the androgen receptor gene of three men with partial androgen insensitivity syndrome", *Clin Endocrinol,* 37(3):214–20, 1992.

Song, Chung, S., et al., "Androgen Receptor messenger ribonucleic acid (mRNA) in the rat liver: changes in mRNA levels during maturation, aging and calorie restriction", *Endocrinology,* 128(1):349–56, 1991.

Song, Chung S., et al., "A Distal activation domain is critical in the regulation of the rat androgen receptor gene promoter", *Biochem. J.,* 294, 1993.

Song, Chung S., et al., "Characterization of Distal Activation and Repressor Domains Critical for Regulation of Rat Androgen Receptor Gene Promotor", *74 Annual Endocrine Society Prog. & Abstracts Abstract,* 1505:428, 1992.

Song, Chung S., et al., "Cloning and Characterization of the Upstream Regulatory Region of the Rat Androgen Receptor Gene", *74 Annual Endocrine Society Prog. & Abstracts Abstract,* 954:289, 1993.

Stoner, Elizabeth, "The Clinical Development of a 5α–Reductase Inhibitor, Finasteride", *J. Steroid Biochem. Molec. Biol.,* 37(3):375–378, 1990.

Tilley, Wayne D. et al., "Expression of the Human Androgen Receptor Gene Utilizes a Common Promoter in Diverse Human Tissues and Cell Lines", *The Journal of Biological Chemistry,* 265(23):13776–13781, 1990.

Trapman, J., et al., "Cloning, Structure and Expression of a cDNA Encoding the Human Androgen Receptor", *Biochemical and Biophysical Research Communications,* 153(1):241–248, 1988.

To, Richard Y. –L. and Paul E. Neiman, "The Potential for Effective Antisense Inhibition of Retroviral Replication Mediated by Retroviral Vectors", *Gene Regulation: Biology of Antisense RNA and DNA,* 261–271, 1992.

The Upjohn Company, Rogaine, "The Only Product Ever Proven to Regrow Hair", 1992.

Vinson, C. R., "Scissors–grip model for DNA recognition by a family of leucine zipper protein", *Science,* 246:911–16, 1989.

Yarbrough, W. G., et al., "A single base mutation in the androgen receptor gene causes androgen insensitivity in the testicular feminized rat", *J Biol Chem,* 265(15):8893–8900, 1990.

Dialog Search Report dated Dec. 9, 1992 (8:56 a.m.).
Dialog Search Report dated Dec. 9, 1992 (9:07 a.m.).
Dialog Search Report dated Dec. 9, 1992 (10:33 a.m.).
Dialog Search Report dated Jan. 26, 1994.

```
-2656  CCATAGTGGACCACTGTAGTCAATCTTCC
-2626  CCATCATGATATAATTTGTGAAAGTTTGTTTCACTTTGGAAGTTAAAAAAAATCTAGAGACAGCTCAATCTGGAAAGGT
-2546  CTCAGTAGCCAACCTGAGGGCCTGAGCCCAGCACACACATAAATAAAAAGCCAGGAAAGGCACTGCATACTT
-2466  TTAATCCCAACATTGCAGAGAGAGACAAGTAGATCTCTGAGACTCACTGACCAGCCAGCCTACCCTACACATGATGAATT
-2386  CGAGGACAGTGAAAGACCCTGTAAAAAGAAACATTTGGGTGGTGGCTGATGAACGACATTCATAGTAACACAGTATTCC
-2306  TTTGGCCTTCGTGTGTGTGTGTGTGTGTGTTTCTCTGTGTTCTCTGTGAAAGAGAGATCCTTCCAACTTTTAGAATGCTTCCTT
-2226  CTCTGTGTGTTTCTCTGTGTGTTCAGTCCCTGCAGCCTTCTGAGGGAGGTATTTTTAGTTTCAATTTT
-2146  ATTCACAAATTGCTTTTATACATTGGATCTGTTTCAGTCCCTGCAGCCTTCTGAGGGAGGTATTTTTAGTTTCAATTTT
-2066  CTGTGAGGATATCTGTAAAGACAACTTTGATGCTGTGGAAACAACTTAGGCTTCAGATTTTCACTCCTGTGTTTGAATC
-1986  TGTATAGTGCTTTCAGCTATGGAAAGCTGAATCATTTTCCTGTTCATTTTTCTGTTCAGTCTATAAAAGAGAATAATCCTCCTGGC
-1906  TTTCCTTTTGCCATTGTTTATTCACTGCTATTAGCCCCTCTCTTTCATTGTCAGTCTATAAAAGAGAATAATCCTCCTGGC
-1826  TCTGAGACATACGTTCATTCTAGTCTACCACTTTGCCTGTGCATTCAATTCCCTTGGACTAAAACCATTCAAAAGCTTTG
-1746  GTAGATGTGAGGCTGTAATGACTATTCAAATAGGGTCTTCAAAGTATCTGTGCGTTTTGAAACACTTCACTAGAATAGTG
-1666  AAAAATTAGCCATTTTACAGTTTGTCAGTTTTGAATAACTTTGCTTTTTTTTTTTTGGACCCTACGGAGTGATTT
-1586  GTGAAACTAAGCAAAAAGCAATACAATAAGGCCTCAGCTGCTATCCTTACAGCAGATAATTTTTCACCTGG
-1506  GCAGGAGGAAGCACTCTCAGGTCATTTTGTTCTAAACATTCATGCTGTTTCCAAGGGTTGTGGACCTGCTGATGAGA
-1426  GCACAACTAATGTAGAAAAAACCTGGAAAGTTTATGTTCTGCTAACATGGGAACATAACAATGTCCTTGCTTCACTTCT
-1346  TTATCTGTGAAACAGAGTTGATCATGCATACTGCTTTTTTCCCTTGAGGTTTCAGTTAACTCCTTCAGTCAAGGTAAA
```

Fig. 1A

```
-1266  CCCTCAGTATAATGGAGAAAGCCCTCCCCCTCACTGTAGAGGCCTGTAAATGTGGAAATGGCTGGTATGATTGCATAGTC
-1186  CACCAAACCCAGAATTTCAGAAGCTGAATCAGAAGGATCAGAGTTCAAGATCTGTGGGGGTATGAAACAAATCCCTA
-1106  TCTCAAAAGAAAGATAAAATGACTCCCTCCTCCCCAAATACCCATTCTTTTACTTGCTGGGACAGATCTAGAGGTATAA
-1026  AGTCTTTTACAAGTGCTGGGGTCTACAGCCTTTCTCTCTAAGGACATATTTCTCTATAGGTCTACTCTTGATCTTTCTATTGC
 -946  TCTTTTGTCTTTGGGAATATCCTACATCATCTCTGTTCAACCTGTCCATTAAAGAAAGATCAGCCCTC
 -866  TGTGATTTCTCTACCCAGGATAAGAATTTTCAAGTGCAAACAATTTGGACATCTAAAGGCTTCTATACAAACAACACTTT
 -786  GGACAAAATCGAAGGTTCATGTGTGCATGACAACAGTGTTTTTGACATTTGTGTTTGCACACTGTCTGAGTGATTTTTTG
 -706  CCTTTGCAAATCTGGAGAAATCAAACAGTGTAAGTTACAGGCAATTCCCAACAGAAAGAAGGCAAGAAATGAGGTAGAA
 -626  ATGACCACTGGCTTCTTGGGCCCAGAGAGTTGCTTTGGTGTCGGAATTCCCCATCTACGCTACTGGAGG
 -546  ATCTCAAAGGTTTCTGCAAGAGGGTACCTAAGAACAATTGGTAGCCGGTACTTCTCAATGCCCCTTCTCCCCTCGGAGAATCTGT
 -466  GTGGGCCCTGGGGGAGAGGGTACCTAAGAACAATTGGTAGCCGGTAGGCTTGTCTGTTAAAAAATCGC
 -386  TTTGGGATTGGGTTCAGGAATGAAATCCGGCCTAAGCCCGGTTCCGAAAAACAAGTGGTATTTGGGGAAAAGGGGTCTTCAGA
 -306  TCCAAGTTAAAGCTTCTGCTTTGGAGTCTCAACCATTCCAACCATACTACGCCACGACTATGTTCTCTAAAGCCACCTGCCTACGTTGCGG
 -226  GGCTACAGGAGTCCTTCCAACCATTACGCCACGACTATGTTCTCTAAAGCCACCCTGCCTACGTTGCGG
 -146  TGAGGGGAGGGGAGAAAAGGGGAAAAGGGGAGAGGGAAAAGGGGAGAGGGAAAAGGAGTGGGAAGGCAGGG
  -66  AGGCCGGCGGGGGGACCCTGTTTCGTTTCCACCTCCCAGCCCCCTGCCCCGAGATCCCTAGGA
                                                                    →
                                                                   +1
  +15  GCCAGCCTGCTGGGAGAACCAGAGGGTCCGGAGCAAACCTGAGAGGCTGAGAGGGCATCAGAGGGGAAAAGACTGAGCTAG
  +95  CCACTCCAGTGCCATACAGAAGCTT
```

Fig. 1B

Cis-element 5'-CTCTTGATCTTTCTATTGCTCTTTTG-3'
3'-GAGAACTAGAAAGATAACGAGAAAAC-5'
TFO 5'-GTGTTGTTGTTTGTTTTGGTGTTTTG-3'

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 2775 base pairs
        ( B ) TYPE: nucleic acid
        ( C ) STRANDEDNESS: single
        ( D ) TOPOLOGY: linear ( i i ) MOLECULE TYPE: oligonucleotide ( i i i ) SEQUENCE DESCRIPTION: SEQ ID NO:1:

```
CCATAGTGGG  ACCACTGTAG  TCAATCTTCC  CCATCATGAT  ATAATTTGTG  AAAGTTTGTT    60
TCACTTTGGA  AGTTAAAAAA  AATCTAGAAG  ACAGCTCAAT  CTGGAAAGGT  CTCAGTAGCC   120
AACCTGAGGG  CCTGAGCCTG  AGCCCAGCA   CACACATAAA  TAAAAAGCCA  GGGAAAGGCA   180
CTGCATACTT  TTAATCCCAA  CATTGCAGAG  AGAGACAA    GTAGATCTCT  GAGACTCACT   240
GACCAGCCAG  CCTACCCTAC  ATGATGAATT  CGAGGACAGT  GAAAGACCCT  GTAAAAGAA    300
ACATTTTGGG  TGGTGGCTGA  TGAACGACAT  TCATAGTAAC  ACAGTATTCC  TTTGGCCTTC   360
GTGTGTGTGT  GTGTGTGTGT  GTGTGTGTGT  GTGTGTGTGT  GTGTGTGTGT  GTGTGTTTCT   420
CTGTGTGTTT  CTCTGTGTGT  TTCTCTGTGT  GTTTCTCTGT  GTGTTTCTCT  GTGTAAAGAG   480
AGATCCTTCC  AACTTTTAGA  ATGCTTCCTT  ATTCACAAAT  TGCTTTTATA  CATTGGATCT   540
GTTTTCAGTC  CCTGCAGCCT  TCTGAGGGAG  GTATTTTAG   TTTCAATTTT  CTGTGAGGAT   600
ATCTGTAAAG  ACAACTTTGA  TGCTGTGGAA  ACAACTTAGG  CTTCAGATTT  TTCACTCCTG   660
TGTTTGAATC  TGTATAGTGC  TTTCAGCTAT  GGAAAGCTGA  ATCATTTTC   CTGTTCATTT   720
TTCTGAATTT  CCTCTCTACA  ACCTTCCCTC  TTTCCTTTTG  CCATTGTTTA  TTCACTGCTA   780
TTAGCCCTCT  CTTTCATTGT  CAGTCTATAA  AAGAGAATAA  TCCTCCTGGC  TCTGAGACAT   840
ACGTTCATTC  TAGTCTACCA  CTTTGCCTGT  GCATTCAATT  CCCTTGGACT  AAAACCATTC   900
AAAAGCTTTG  GTAGATGTGA  GGCTGTAATG  ACTATTCAAA  TAGGGTCTTC  AAAGTATCTG   960
TGCGTTTTGA  AACACTTCAC  TAGAATAGTG  AAAAATTAGC  CATTTACAG   TTTGTCAGCT  1020
TTTGAATAAC  TTTGCTTTTT  TTTTTTTTT   TGGACCCTAC  GGAGTGATTT  GTGAAACTAA  1080
GCAAAAAGCA  ATACAATAAT  CACAATAAGG  CCTCAGCTGC  TATCCTTACA  GCAGATAATT  1140
TTTCACCTGG  GCAGGAGGAA  GCACTCTCAG  GTCATTTGT   TCTAAAAGAT  TACTTCATGC  1200
TGTTTTCCAA  GGGTTGTGGA  CCTGATGAGA  GCACAACTAA  TGTAGAAAAA  ACCTGGAAAG  1260
```

```
TTTATGTTCT GCTAACATGG GGAACATAAC AATGTCCTTG CTTCACTTCT TTATCTGTGA   1320
AACAGAGTTG ATCATGCATA CTGCTTTTTT TTCCCTTGAG GTTTCAGTTA ACTCCTTCAG   1380
TCAAGGTAAA CCCTCAGTAT AATGGAGAAA GCCCTCCCCC TCACTGTAGA GGCCTGTAAA   1440
TGTGGAAATG GCTGGTATGA TTGCATAGTC CACCAAACCC AGAATTTCAG AAGCTGAATC   1500
AGAAGGATCA TGAGTTCAAG ATCTGTCTGG GGTATGAAA CAAATCCCTA TCTCAAAAGA   1560
AAGATAAAAT GACTCCCTCC TCCCCCAAAT ACCCATTCTT TTACTTGCTG GGACAGATCT   1620
AGAGGTATAA AGTCTTTTAC AAGTGCTGGG GTCTACAGCC TTTCTCTAAG GACATTTTCT   1680
CTATAGGTCT ACTCTTGATC TTTCTATTGC TCTTTTGTCT TTACAGTTGG GAATATCCTA   1740
CATCATATTC ATCTGTTCTA ACCTGTCCAT TAAAAGAAAG ATCAGCCCTC TGTGATTTCT   1800
CTACCCAGGA TAAGAATTTT CAAGTGCAAA CAATTTGGAC ATCTAAAGGC TTCTATACAA   1860
ACAACACTTT GGACAAAATC GAAGGTTCAT GTGTGCATGA CAAGTGTTTT TGACATTTGT   1920
GTTTGCACAC TTGTCTGAGT GATTTTTTTG CCTTTGCAAA TCTGGAGAAA TCAAACAGTG   1980
TAAGTTACAG GCAATTCCCA ACAGAAAGAA GGGCAAGAAA TGAGGTAGAA ATGACCACTG   2040
GCTTCTTGGG CCCAGAATTC CCAGAGTAAA TGGCTTGGTG TCGGGAATTC CCCATCTACG   2100
CTACTGGAGG ATCTCAAAGG TTTCTGCAAG AGTTGCTTTG GCTGCAGCTT GTTCTTTAAT   2160
CTCTTGGGAC TCTCCCTTCT GCTTGTCCTG GTGGGCCCTG GGGAGAGGG TACCTAAGAA    2220
CAATTGGTAG CCGGTACTTC TAATGCCCCT TCCTCCCTCG GAGAATCTGT TTTGGGATTG   2280
GGTTCAGGAA TGAAATCCGG CCTGTGCTAA CCTTTTGAGG AGCCGGTAGG CTTGTCTGTT   2340
AAAAATCGC TCCAAGTTAA AGCTTCTGCT TTGGAGTCTA AAGCCCGGTT CCGAAAAACA    2400
AGTGGTATTT GGGGAAAAGG GGTCTTCAGA GGCTACAGGG AGTCCTTCCA GCCTTCAACC   2460
ATACTACGCC ACGACTATGT TCTCTAAAGC CACCCTGCGC TACGTTGCGG TGAGGGGAGG   2520
GGAGAAAAGG AAAGGGGAGG GGAGGGGAGG GGAGGGGAGG GGAGAGAGGA AAGGAGGTGG   2580
GAAGGCAGGG AGGCCGGCGG GGGCGGGACC GACTCACAAA CTGTTGCATT TCGTTTCCAC   2640
CTCCCAGCGC CCCCTCGGAG ATCCCTAGGA GCCAGCCTGC TGGGAGAACC AGAGGGTCCG   2700
GAGCAAACCT GGAGGCTGAG AGGGCATCAG AGGGGAAAAG ACTGAGCTAG CCACTCCAGT   2760
GCCATACAGA AGCTT                                                    2775
```

( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: oligonucleotide ( i i i ) SEQUENCE DESCRIPTION: SEQ ID NO:2:

```
CAAAGAGCA ATAGAAAGAT CAAGAG                                           26
```

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: oligonucleotide ( i i i ) MOLECULE TYPE:

( i v ) SEQUENCE DESCRIPTION: SEQ ID NO:3:

GTGTTGTTGT TTGTTTTGGT GTTTTG 26

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: oligonucleotide ( i i i ) SEQUENCE DESCRIPTION: SEQ ID NO:4:

CAAAAGAGCA ATAGAAAGAC T 21

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: oligonucleotide ( i i i ) SEQUENCE DESCRIPTION: SEQ ID NO:5:

TGTATCTTAT GGTACTGTAA CTG 23

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: oligonucleotide ( i i i ) SEQUENCE DESCRIPTION: SEQ ID NO:6:

CTTTATGTTT TTGGCGTCTT CCA 23

( 2 ) INFORMATION FOR SEQ ID NO:7:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: oligonucleotide ( i i i ) SEQUENCE DESCRIPTION: SEQ ID NO:7:

TTTTGTTGTT GTTGTTGTGG GGTTTT 26

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: oligonucleotide ( i i i ) SEQUENCE DESCRIPTION: SEQ ID NO:8:

GTTTTCTCGT TATCTTTCTA G 21

METHODS AND COMPOSITIONS RELATING TO THE ANDROGEN RECEPTOR GENE AND USES THEREOF

The government owns rights in the subject matter of the claimed invention as research was funded by NIH grants R01-AG- 63527 NIH grant P01-AG 06872, and NIH grant R 37-DK 14744.

BACKGROUND OF THE INVENTION

1. Field of the Invention

The present invention relates generally to the fields of hormone receptors and drug design. More particularly, it concerns the androgen receptor, methods for regulating androgen receptor gene expression, rational drug design through specific antisense and antigene technology, and also provides specific compositions, including pharmaceutical agents, for use in inhibiting the expression of the androgen receptor gene and treating related pathologies such as prostatic hypertrophy and androgenetic alopecia.

2. Description of the Related Art

Regulated function of hormonal agents play a critical role in health and disease. Target cell responsiveness to a hormonal signal is a product of both the cellular concentrations of the hormone ligand and the actions of its specific receptor protein. Disease conditions such as androgen-dependent prostatic hypertrophy and neoplasia are a result of the aberrant actions of steroid hormones. The design of drugs for the treatment of these conditions is now feasible through the use of modified steroid ligands that act either as receptor agonist/antagonist or as enzyme inhibitors. However, a major problem inherent to 'receptor-fitting' drug design is cross-reactivity of the ligand agonist/antagonist to related receptors and the consequent side effects.

The androgen receptor (AR) is a member of the ligand-dependent transcription factor superfamily. The ligand-dependent transcription factor superfamily includes, the steroid hormone receptors, the thyroid hormone/retinoid/vitamin D receptors, the receptors for certain xenobiotic agents and related orphan receptors (Evans, 1988; O'Malley, 1990; Isseman & Green, 1990). Information on the regulation of most of the steroid receptor genes, including the gene for AR, is rather sparse (Baarends et al., 1990; Tilley et al., 1990; Encio et al., 1992; Huckaby et al., 1987; Leclerc et al., 1992). Delineation of upstream regions and transcriptional factors that regulate the expression of the androgen receptor gene will narrow this gap, and aid in understanding the interplay of various transcription factors in tissue-specific expression of the AR gene.

The androgen receptor (AR) gene is expressed at high levels in various reproductively relevant cell types, and plays a pivotal role in the development and maintenance of sex functions. The AR gene is also expressed in many non-reproductive tissues including brain, liver, kidney and bone marrow (Milin & Roy, 1973; McEwen, 1980; Pajunen et al., 1982; Colvard et al., 1989; Song et al., 1992). The AR regulates a number of enzymes and proteins in both reproductive and non-reproductive tissues. Aberrant regulation of the AR gene is associated with reproductive abnormalities such as the androgen insensitivity syndromes. Abnormal regulation of the androgen receptor gene is also believed to be important in prostatic hypertrophy and neoplasia (Pinsky & Kaufman, 1987; Coffey & Pienta, 1987; Yarbrough et al., 1990; Newmark et al., 1992).

The etiology of androgen dependent alopecia has also been traced to androgen dysfunction (Neil S. Sadik and Donald Charles Richardson, *Your Hair, Helping to Keep It*, Consumer Reports Books, editors and publishers, Yonkers, N.Y., 1992). Androgenetic alopecia, also known as male pattern baldness, is observed in both men and women, and is statistically the most common form of hair loss in men. Commercial preparations for controlling hair loss occupy a large market in the United States, with several billion dollars spent annually on hair loss prevention treatments. Rogaine® is a prescription preparation currently used to prevent hair loss and includes the active ingredient, minoxidil. This treatment controls hair loss primarily by enhancing blood circulation to the treated area. However, limited success with such agents has been reported.

Relatively little is known regarding the regulation of AR gene expression or function. The sequence of the androgen receptor complementary DNA has been determined (Lubahn et al. (1988) and Chang et al. (1988)). Marcelli et al. (1990) have demonstrated a correlation between a defect at position 772 of the androgen receptor gene and decreased androgen receptor gene and mRNA function. However, the sequence for the AR gene promoter has not been characterized beyond nucleotide position −570, and no specific upstream promoter regions or binding sites for transcription factors have been demonstrated.

The promoter regions of eukaryotic genes generally contain polypurine/polypyrimidine regions that are the preferred sites for the binding of transcription factors. Polypurine-polypyrimidine stretches are also candidates for triple helix formation with single-stranded oligonucleotides through Hoogsteen base pairing (Durland et al., 1992). Formation of a triple helix disrupts the upstream interaction of transcriptional factors thereby affecting gene expression. Oligonucleotide directed modulation of gene transcription by triple helix forming oligonucleotides (TFOs) is a feasible method for attenuating several genes with important regulatory functions such as c-myc, EGF receptor and interleukin-2 receptor (Durland et al., 1992; Bino et al., 1993; Grigopiev et al., 1992).

The lack of specificity prevalent in receptor-fitting approaches can potentially be overcome by antisense nucleic acid drug design directed at promoter regions. Antisense nucleic acids may take the form of small oligonucleotides that enter cells through, for example, receptor mediated endocytosis. This approach offers the advantage of being highly specific and relatively non-toxic even at very high concentrations. Use of these technologies has not been applied to regulating androgen receptor gene expression, or in pathologies that relate to the expression of the androgen receptor gene, such as prostatic hypertrophy and androgenetic alopecia.

The lack of knowledge of steroid receptor gene promoter sequences has prevented the realization of the enormous potential of screening and treatment techniques related to altered function of the androgen receptor gene. The identification of critically important regions of the androgen receptor gene promoter would provide information useful in the development of potent and specific oligonucleotide and antisense screening techniques and therapies not currently available.

SUMMARY OF THE INVENTION

The present invention addresses these and other drawbacks in the prior art by providing compositions and methods for the specific inhibition of the androgen receptor gene.

Particularily disclosed are oligonucleotides of defined sequence capable of regulating the transcription of the androgen receptor gene by specifically interacting with its promoter sequences.

As used in the description of the present invention, specific interaction with the promoter sequence of the androgen receptor gene is defined as the affinity of the oligonucleotide for binding to the promoter sequence of the androgen receptor gene without substantial binding to non-promoter sequences of the androgen receptor gene.

The oligonucleotides of the present invention are generated in view of information disclosed by the inventors regarding two critical upstream regions, one located between positions −960 (position 1697 of SEQ ID NO:1) and −940 (position 1717 of SEQ ID NO:1) and the second between positions −140 to −90 of the rat androgen receptor gene promoter region (FIGS. 1A–1B). As these regions are likely to be highly similar to the human AR gene sequence, the inhibition of human AR gene transcription and expression is also encompassed by the present invention.

The present inventors have conducted significant studies into the structure, function and regulation of the AR gene. A genomic clone of the rat androgen receptor (rAR) gene containing approximately ten kilobases of the 5' flanking region is disclosed in the present invention. The nucleotide sequence of this clone up to −2656 from the start site of translation has also been established (FIGS. 1A–1B, SEQ ID NO:1). During structure-function analysis of the 2.6 kilobase pairs of the upstream promoter of the AR gene, the present inventors detected the critical activation domain within a specific 21 base pair (bp) region at a distal promoter region of the AR gene.

The upstream promoter region of the AR gene is further defined as an activation region, and has a nucleic acid sequence that corresponds to a sequence located at positions −960 (position 1697 of SEQ ID NO:1) to −940 of the rat androgen receptor gene promoter region. The upstream region may be employed in characterizing androgen receptor gene transcription. This region may also potentially be useful as a diagnostic tool in genetic screening for the androgen receptor gene, and for screening for pathologies involving androgen receptor gene dysfunction.

Transfection analysis of progressively deleted AR gene promoter fragments directing the expression of a reporter gene (firefly luciferase) have been performed that demonstrate the existence of the critical upstream promoter region located between position −960 (position 1097 of SEQ ID NO:1) and −572 (position 2085 of SEQ ID NO:1) of the rat androgen receptor gene. The significant importance of this region is demonstrated by the greater than 90% decrease of AR promoter activity that occurred by deletion of this region (FIG. 2). This profound inhibition demonstrated that this region is of tremendous importance in the regulation of androgen receptor gene expression.

The present invention in a preferred embodiment includes oligonucleotides for regulating the androgen receptor gene having a nucleic acid sequence that binds to an upstream activator promoter region of the androgen receptor gene. The oligonucleotides have a nucleic acid sequence that binds specifically to a critical upstream region, referenced herein as specifically an upstream activation region (UAR), of the androgen receptor gene promoter region (AR-PR) of the androgen receptor gene. The invention anticipates the use of oligonucleotides for regulating androgen receptor gene transcription and expression of the human and rat androgen receptor gene. In the rat, the upstream activation region is located between nucleotide positions −960 and −940 of the rat androgen receptor promoter sequence. The oligonucleotides may be further defined as having a nucleic acid sequence corresponding to position 1697 to 2087 of SEQ ID NO:1, and having specific binding affinity for a UAR between nucleotide positions −960 and −940 of the rat androgen receptor promoter region (AR-PR). In still another embodiment, the oligonucleotide may be described as having a nucleic acid sequence defined by position 1697 to 1992 of SEQ ID NO:1, wherein the oligonucleotide has specific binding affinity for a UAR between nucleotide positions −960 and −665 of the rat AR-PR. Another embodiment of the oligonucleotide is defined as having a nucleotide sequence defined by position 1697 to 1902 of SEQ ID NO:1, having specific binding affinity for the UAR between nucleotide positions −960 and −755 of the rat AR-PR.

In still another embodiment, the oligonucleotide has a sequence defined as position 1697 to 1801 of SEQ ID NO:1, and may be described as having specific binding affinity for a UAR between nucleotide positions −960 and −852 of the rat AR-PR. Even more particularly, the oligonucleotide may be defined as having the sequence at position 1697 to 1730 of SEQ ID NO:1, and as having specific binding affinity for a UAR between nucleotide positions −960 and −927 of the rat AR-PR.

The upstream activation region of the invention is further defined as corresponding to the nucleotide sequence located at positions −960 to −940 of the rat androgen receptor gene promoter region. The upstream activation region may be employed in characterizing androgen receptor gene transcription, and may also potentially be useful as a diagnostic tool in pathologies involving androgen receptor gene dysfunction.

In another aspect of the invention, triple helix forming oligonucleotides (TFOs) specific for the androgen receptor gene promoter region are disclosed. The physiological formation of a triple helix is related to localized polypurine/polypyrimidine regions and not to their orientation, hence oligonucleotides complementary to either strand are contemplated. Accordingly, the oligonucleotides of the present invention are directed to this region of the androgen receptor gene promoter and are capable of modulating androgen receptor gene expression through binding to this region of the promoter, thereby affecting AR gene transcription.

The oligonucleotides and TFOs of the present invention may be advantageously formulated for use as medicaments and pharmacologically active preparations for the treatment of androgen related gene pathologies such as male pattern baldness and prostatic hypertrophy.

The oligonucleotides of the invention may be further described as a single stranded oligonucleotide of deoxy ribonucleic acid (DNA). Although the inventors also contemplate the possible use of single stranded ribonucleotides, it is likely that these ribo-oligonucleotides will be rapidly degraded and therefore have reduced efficacy. In addition, it is contemplated that modifications and substitutions of the various nucleotide sequences of the oligonucleotides may be made in the preparation of still other embodiments of the invention with retained functionality for binding the activation region of the androgen receptor gene promoter, and thereby provide inhibition of the gene, apart from and in addition to the nucleotide substitutions and modifications specifically exemplified in the examples.

The modulation of AR gene transcription through the formation of TFO's, in a preferred embodiment, is provided where the oligonucleotide binds to the androgen receptor gene only in a transcriptionally activating region of the AR-PR. This particular oligonucleotide has a nucleotide sequence defined by position 1697 to 1717 of SEQ ID NO:1, and as having specific binding affinity for a UAR between nucleotide positions −960 and −940 of the rat AR-PR. The various oligonucleotide segments of the present invention are demonstrated to correspond to a critical UAR of the rat androgen receptor gene promoter, and likely correspond to critical UAR's in the human AR gene. Thus, according to one aspect of the invention, a double-stranded upstream region critical in androgen receptor gene transcription and expression is provided. The upstream region of the present invention in a particularily preferred embodiment is defined as the following double stranded sequence:

5' - CTCTTGATCTTTCTATTGCTCTTTTG-3' (position 1692 to 1717 SEQ ID NO:1)
3' - GAGAACTAGAAAGATAACGAGAAAAC-5' (SEQ ID NO:2)

In still another embodiment, the oligonucleotide may be defined as a 21-base pair segment of nucleic acid, having the sequence:

5'-GATCTTTCTATTGCTCTTTTG-3' (position 1697 to 1717, SEQ ID NO:1)
or its complement:
3'-CTAGAAAGATAACGAGAAAAC-5' (SEQ ID NO:4)

The physiological formation of a triple helix is related to localized polypurine/polypyrimidine regions and not to their orientation, hence oligonucleotides complementary to either strand are contemplated. In another aspect of the invention, TFO's are designed to further enhance the formation of a triple helix specifically at the UAR of the AR-PR. The triple helix forming oligonucleotide (TFO) may be further described as binding a rat androgen receptor gene promoter region between nucleotides −965 and −940. The TFO comprises a single strand of deoxyribonucleotides. In a preferred embodiment, the TFO is defined by a sequence:

5'-GTGTTGTTGTTTGTTTTGGTGTTTTG-3' (SEQ ID NO:3).

This 26 base pair TFO corresponds to the nucleotide sequence of the rat androgen receptor gene promoter region between nucleotides −965 and −940. In a more preferred embodiment, the TFO is a 21 base pair segment having a sequence:

5'-GTTGTTTGTTTTGGTGTTTTG-3' (position 6 to 25, SEQ ID NO:3).

The oligonucleotides of the present invention may be modified so that at least one of the cytosine nucleotides of the sequence is modified to include a methyl group. Methylation of cytosine will enhance the stability of the triplex structure, thus enhancing its expected activity in vivo. The TFO sequence may also be modified to include at least one methylated guanine. However, methylation of guanine in the sequence is not expected to be of significant consequence for stabilizing triplex formation with the AR gene promoter.

In most preferred aspects of the invention, a cholesterol moiety is attached to at least one of the nucleotides of the oligonucleotide sequence. Most preferably, the cholesterol moiety is to be attached to at least one of the nucleotides, preferably a terminal nucleotide, of the sequence. However, the cholesterol moiety may be located at any of the nucleotide sites of the sequence according to the present invention with expected stability-enhancing effects. Cholesterol attachment will enhance cellular uptake of the oligonucleotide. However, other alternative chemical modifications and molecules that have the effect of enhancing cellular uptake of the oligonucleotides may also be employed in the practice of the present invention.

These oligonucleotides are more specifically defined as including between about 50 and about 12 base pairs. In preferred embodiments, the oligonucleotide will include a segment of nucleic acid having between about 26 and about 21 base pairs. A particularily preferred embodiment is an oligonucleotide having 21 base pairs at position −960 to −940 of the androgen receptor promoter. The oligonucleotide having 21 base pairs may be further defined as the 21 base pair sequence from position 1697 to 1717 of SEQ ID NO:1. In a most preferred embodiment the oligonucleotide is designed to enhance triple helix formation and may be further defined as a 26 bp TFO corresponding to SEQ ID NO:3.

As shown in the present disclosure, phosphorothioate derivatives of single stranded oligomers complementary and anti-parallel to the polypurine strand of the androgen receptor gene promoter region effectively inhibit the in cellulo transcription of promoter-reporter constructs containing the rAR gene promoter. Therefore, it is expected that similar constructs may be employed to reduce androgen receptor gene expression in whole organisms having cells with the AR gene, thus providing effective treatments for pathologies characterized by an overexpression of the androgen receptor gene. As used in the description of the present invention, the term in cellulo is defined as pharmacological activity within an intact cell. This definition is distinguished from the term in vitro, the latter connotating chemical activity in systems that do not represent an intact cell. In this regard, in vitro assays demonstrate isolated chemical and biochemical reactions. The in cellulo results disclosed in the present specification demonstrate that the oligonucleotides and TFOs would be effective in inhibiting androgen receptor gene expression in intact cells, and therefore would be expected to inhibit androgen receptor gene expression in intact cells having the androgen receptor gene in an animal.

Various chemical modifications of the triple helix forming oligonucleotide (TFO) may be used for the development of even more sensitive and biologically stable anti-AR TFO. The human androgen receptor gene promoter can also be cloned and characterized for the design of even more specific anti-androgen gene therapeutic agents.

The present invention also provides methods for inhibiting androgen receptor gene expression in a cell having an androgen receptor gene. The described method is expected to provide inhibition of androgen receptor gene expression in hair follicle cells, prostate tissue cells, liver cells, kidney cells, cervical cells, breast tissue cells, as well as other cells that include the androgen receptor gene. In one embodiment, the method comprises administering to a cell having an androgen receptor gene a pharmacologically effective amount of an oligonucleotide having a sequence complementary to an androgen receptor gene promoter region between nucleotides −960 and −940, and thus inhibiting expression of the androgen receptor gene. The oligonucleotide of the method is most preferably defined as comprising a 21 base pair oligonucleotide corresponding to position −960 to −940 (1697 to 1717 of SEQ ID NO:1). However, it is anticipated that the 26 base pair TFO described at position −965 to −940 (1692 to 1717 of SEQ ID NO:1) will be equally efficacious in the described treatment, as well as the 21 base pair TFO defined as SEQ ID NO:4.

Preferably, the oligonucleotides of the invention will be modified to include a cholesterol moiety on at least one nucleotide of the sequence. Most preferably, the cholesterol moiety should be affixed to a terminal nucleotide of the sequence. By way of example, cholesterol hydrogen phosphorate may be used to introduce the cholesterol moiety at the 5' end of the oligonucleotide. After synthesis of the oligonucleotide, the cholesterol moiety would be added to the 5' end using the standard synthesis cycle (Applied Biosystems).

In still another embodiment of the invention, a method for treating androgen dependent hair loss in a patient, particularly a male patient, is described. The method comprises identifying a patient having androgen-dependent hair loss and applying a pharmaceutical preparation containing a pharmacologically active amount of an oligonucleotide having a sequence corresponding to position –960 to –570 or a fragment thereof in a pharmaceutically acceptable carrier. Most preferably, the oligonucleotide comprises a triple helix forming oligonucleotide having a sequence defined in SEQ ID NO:3, and is modified with a cholesterol moiety.

A patient having androgen dependent hair loss may be selected on the basis of evidence of male-pattern baldness of the scalp and the relative concentration of androgen determined to exist in a biological sample, such as blood, obtained from the patient. By comparing the androgen level obtained from the patient to an androgen level determined to constitute an average control androgen level, patients likely to benefit from the treatment may be selected.

Androgen concentrations may be determined with radio-immunoassay measurement of testosterone, a technique well known to those of skill in the art.

In a most preferred embodiment of the proposed method, pharmaceutical preparations containing a concentration of one or more TFO(s) of between about 0.1 mg/ml and about 1.0 mg/ml may be employed. Such a preparation can be formulated for topical application, and would be applied to the areas on the patient affected with the androgen-dependent hair loss. The frequency and amount of application of the medicament would vary according to the regimen prescribed by the attending physician. A treatment regimen comprising a twice daily application of a pharmaceutical preparation including the cholesterol modified TFO at a concentration of between about 0.01 mg/ml and about 0.1 mg/ml should decrease androgen receptor gene expression in the cells of the scalp of the patient, and thereby provide a beneficial therapeutic treatment to the patient.

The pharmaceutical preparations including the oligonucleotides, and specifically the TFOs of the invention, may be formulated according to any of those techniques well known to those of skill in the pharmaceutical arts. For example, techniques employed for the preparation of such topical preparations are described in Remington's Pharmaceutical Sciences, (18th ed.) (1990), which reference is specifically incorporated herein by reference for the purposes of general teachings regarding the formulations of pharmaceutical agents, i.e., carriers, fillers, stabilizers, etc. The oligonucleotide cholesterol ester may be added to a lanolin based hair cream at a concentration and dose as described above.

Transactivation through the upstream region of the androgen receptor gene is demonstrated by the present inventors to be mediated by a novel nuclear protein. Presence and activity of this novel nuclear protein is evidenced in the gel shift analysis results disclosed herein (FIG. 3), and demonstrate the specific binding activity of the nuclear protein to the upstream activation region of the androgen receptor gene promoter. More specifically, a trans-activating protein that binds to the upstream activating region between positions –960 and –940 of the androgen receptor gene, and that regulates expression of the androgen receptor gene is disclosed. The nuclear protein of the invention has been detected in nuclear extracts from both rat liver and rat kidney, as well as from HeLa cells (a human cervical carcinoma) (see FIG. 4, arrowhead indicates DNA-protein complex binding). This nuclear protein is likely present in all animal cells that have the androgen receptor gene.

The nuclear protein of the present invention may be further defined as a transcription factor important in the expression of the androgen receptor gene. More specifically defined, this protein may be described as binding the AR gene promoter region only between positions –960 and –940 of the androgen receptor gene promoter region. The nuclear protein may be used in the preparation of antibodies specific for the protein. In addition, the protein may also be used to regulate the expression of androgen receptor gene. These are two of the many uses contemplated by the present inventors.

BRIEF DESCRIPTION OF THE DRAWINGS

FIGS. 1A–1B. Nucleotide sequence of the rAR gene promoter from –2656 bp to +119 bp. (SEQ ID NO:1) Bases from +1 to +119 of exon-1 are underlined. The transcription initiation site was established by primer extension analysis with both prostate and seminal vesicle RNAs.

965 oligo

–965 –940

CTCTTGATCTTTCTATTGCTCTTTTG 950 oligo

–950 –918

TTGCTCTTTTGTCTTTACAGTTGGGAATATCCT

Figure 3:
FIG. 3. Gel mobility shift analysis of complexes between nuclear proteins and specific sequence region of the AR gene. The radiolabeled 965 oligo spanning from –965 to –940 bp of the rAR promoter was incubated with bovine serum albumin (lane 1) and with 8 μg of kidney nuclear extracts (lanes 2–4). For competition studies, nonradioactive competitor oligos, i.e., the homologous 965 oligo (lane 3) and an overlapping 950 oligo spanning from –950 to –918 bp of the rAR promoter (lane 4) were used at a 500 fold molar excess. Nucleotide sequences of the 965 (position 1692 to 1717 of SEQ ID NO:1) and 950 (positions 1706 to 1738 of SEQ ID NO:1) oligos are as follows.
Figure 4:
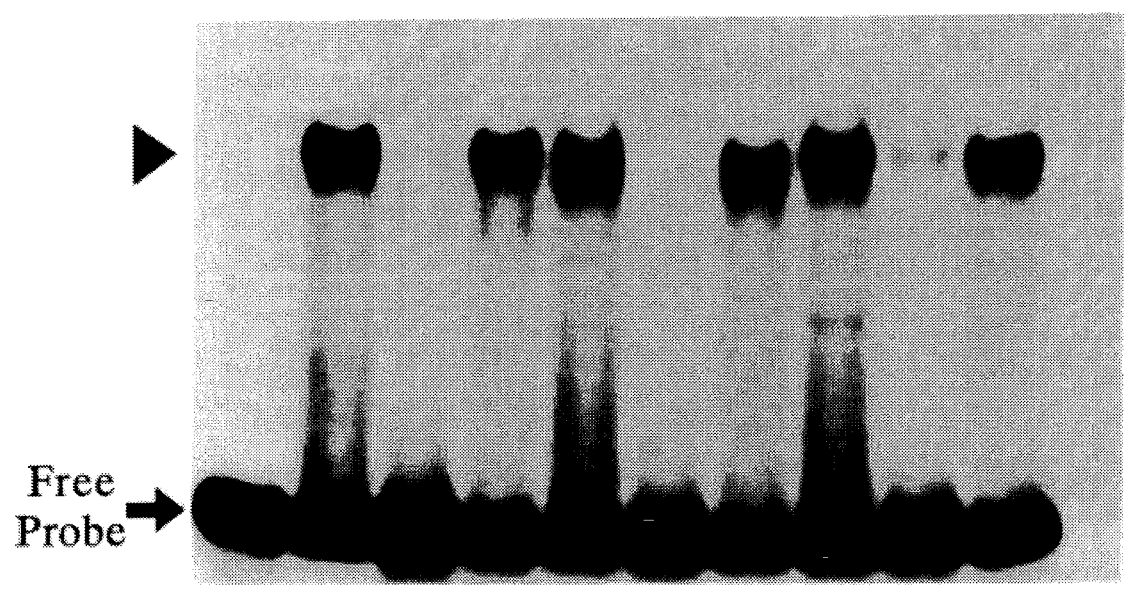

FIG. 4. Gel-shift assay used to detect the presence of a nuclear binding protein having a sequence specific binding activity for the promoter sequence of the rat androgen receptor gene. Several sources of cells were processed to obtain nuclear extracts. A double stranded segment of DNA having a sequence corresponding to the promoter region sequence of the rat androgen receptor gene between nucleotide –960 and –940 was prepared and labeled with $^{32}$P, and used as a probe. This probe is described as the 965 oligo. The "Free Probe" migrated to the bottom of the gel as indicated. The dark arrow-head in the figure indicates the location of the specific DNA-protein complex. The gel demonstrates the wide distribution of a DNA binding protein in these cell preparations that binds to DNA in a sequence specific manner to a sequence corresponding to positions –960/–940 of the rat androgen receptor gene promoter. The 965 oligo was used as the radioactive probe. Sources of nuclear extracts in different lanes are: Rat liver (lanes 2, 3 & 4); Rat kidney (lanes 5, 6 & 7); HeLa cell (lanes 8, 9 & 10); lane 1: bovine serum albumin instead of nuclear extracts. Lanes 2, 5 & 8 represent binding reactions in the absence of competitor DNAs. Homologous competitor oligos were used for lanes 3, 6 & 9. An overlapping 950 oligo was used for lanes 4, 7 & 10. For homologous and heterologous competitions, a 500 fold molar excess of the cold oligo was used. Sequences of the competitor oligos are given in the brief description of FIG. 3.

Figures 5, 6:
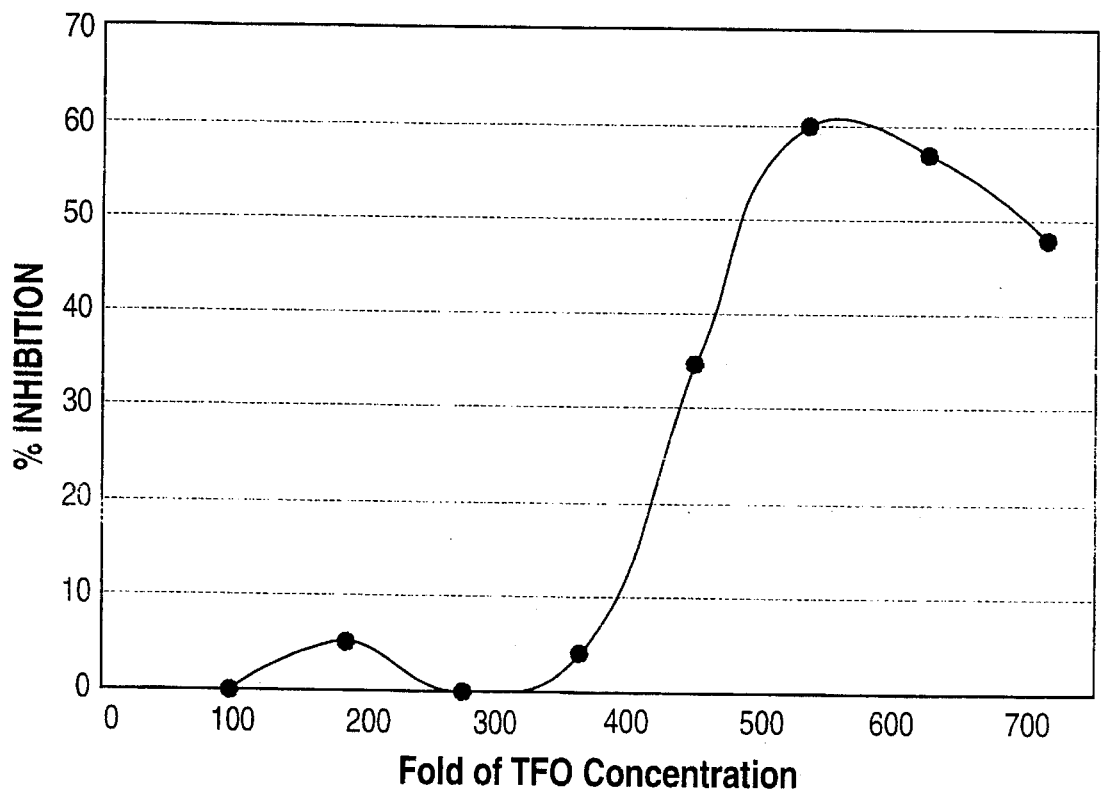

FIG. 5. Sequence of the TFO phosphorothioate corresponding to the critical upstream region of the rAR gene promoter. The 62 corresponding sequence identifiers are; position 1692 to 1717 of SEQ ID NO:1, SEQ ID NO:4, and SEQ ID NO:3.

FIG. 6. Inhibition of rAR promoter activity by the TFO phosphorothioate sequence shown in FIG. 5. The promoter-reporter construct was preincubated with either the complementary TFO or the scrambled oligo followed by transfection into COS1 cells. Differences in the luciferase activity after 20 hours of cell culture were used to compute the percent inhibition.

DETAILED DESCRIPTION OF THE PREFERRED EMBODIMENT

The claimed preparations and methods provide for the specific inhibition of the expression of the androgen receptor gene in cellulo. Consequently, the present invention also provides methods whereby specific androgen dependent pathophysiologies, such as male pattern baldness and prostatic hypertrophy and androgen-dependent cancers, may be treated.

Disclosed herein are results which demonstrate the cloning of the far upstream region of the rat androgen receptor (rAR) gene and its nucleotide sequence up to −2656 base pairs from the start site of translation. Nested deletion mutants of rAR 5' flanking sequences were ligated to the luciferase reporter gene, and their promoter activities were examined in transfected COS1 cells. These results show a critical upstream region located between positions −960 and −940 involved in the activation of gene transcription. Deletion of this upstream region is demonstrated to provide a greater than ten-fold decrease of AR gene promoter activity in cellulo.

A nuclear protein that specifically binds to this 21 nucleotide sequence is also disclosed, and was identified by gel mobility shift analysis. The −960/−940 upstream region of the present invention has no homology to the binding sequence of any known transcription factor. This binding protein is also demonstrated to be present in both rat and human (HeLa) cell nuclear extracts.

The pharmaceutical preparations of the oligonucleotides directed to the particular segment of the androgen receptor gene identified herein are preferably prepared so as to be suitable for topical application to the skin, particularly the scalp. Such preparations may be formulated using techniques well known to those of skill in the pharmaceutical arts. Examples of how such formulations may be prepared are reviewed in Remington's Pharmaceutical Science (18th ed.), which reference is specifically incorporated herein by reference for this purpose. As a topical preparation, the described formulations that include the AR-directed oligonucleotide(s) may be used without risk of those side effects typically attendant the use of cross-reacting systemic preparations. The preparation of an aqueous composition that contains the oligonucleotide as an active ingredient is well understood in the art. Typically, such compositions are prepared either as liquid solutions or suspensions; solid forms suitable for solution in, or suspension in, liquid prior to injection can also be prepared. The preparation can also be emulsified. Upon formulation, solutions will be administered in a manner compatible with the dosage formulation and in such amount as is therapeutically effective.

The present invention also provides highly specific oligonucleotide probes that may be used in the identification of critical regions in the androgen receptor gene promoter. This particular utility constitutes one of many characteristic of the present invention.

The following examples are included to demonstrate preferred embodiments of the invention. It should be appreciated that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

CLONING, CHARACTERIZATION AND SEQUENCING OF THE RAT ANDROGEN RECEPTOR GENE PROMOTER

The present example is provided to demonstrate the manner in which the gene segment encoding the androgen receptor gene promoter sequence beyond nucleotide position −570 (position 2087 of SEQ ID NO:1) was characterized and isolated.

Methods

A λEMBL3 rat genomic library (Sau3AI partial digest, Clontech, Palo Alto, Calif.) was screened with a 444 base pair cDNA probe (Song et al., 1991) corresponding to the N-terminal end of the rat androgen receptor (rAR). From 500,000 plaques, 6 positively hybridizing clones were isolated and purified. Phage DNAs from positive plaques were digested with restriction enzymes and analyzed by Southern blotting. The 6 isolated clones contained overlapping fragments of up to 10 kilobases (kb) of the rAR gene promoter.

Single-stranded DNA sequencing of recombinant M13 mp18 DNAs were carried out in the presence of [$\alpha$-$^{35}$S] dATP$\alpha$S and dideoxy chain terminators (Bankier et al., 1987). Gaps in the internal sequence were filled by successive sequencing of the DNA template using different oligodeoxynucleotide primers which anneal to specific regions of the insert DNA. Overlapping DNA fragments were sequenced and each base was scored at least four times from both DNA strands. The Pustell program (IBI, New Haven, Conn.) was used to analyze the sequence data.

Results and Discussion

Six λ-clones containing inserts of approximately 15 kb were isolated from the rat genomic library using a N-terminal specific rAR cDNA fragment as the probe. One of the clones contained up to −5.7 kb of the 5' untranslated sequence and a second one up to −10 kb. Two clones included the entire first exon, a portion of the second exon and a long (~9 kb) intervening sequence separating the two exons.

Exon-1 of the AR gene encompasses the 5' untranslated region and amino-terminal end of the receptor protein where two distinct transactivation domains of AR are localized. A partial restriction map was developed for the entire 10 kilobases of the rAR promoter. Partial digestions of the 5.7 kb AR promoter (spanning −5.7 kb to + 19 bp) with the individual restriction enzymes Eco RI, Bgl II or Pst I resulted in shorter AR promoter fragments which were examined for promoter functions in transfected cells.

The nucleotide sequence of 2656 bp of the AR gene upstream region is presented in FIGS. 1A–1B. The sequence for 572 bases of the AR gene upstream region had been reported earlier (Baarends et al., 1990; Tiley et al., 1990). The reported sequence within this region is in general agreement with the sequence presented in FIGS. 1A–1B. Discrepancies were noted, however, at 9 different base positions. Analysis of sequence motifs for various transactivating factors within this promoter region was performed with the Signal Scan program (Prestridge, 1992). Similar to what has been observed in the receptor genes for glucocorticoid and progesterone (Encio et al., 1992; Huckaby et al., 1987; Leclerc et al., 1992), no discernible "TATA" and "CAAT" boxes were found in the AR promoter.

The consensus DNA-binding sequences for several known transcription factors (Briggs et al., 1986; Curran & Franza, 1988; Martin et al., 1988; Beato, 1988; Vinson et al., 1989; Biggin & Tijian, 1989; Christy & Nathans, 1989; Klemsz et al., 1990; Ron et al., 1990) have been identified within the AR gene promoter sequence. Half palindrome sites for androgen/glucocorticoid/progesterone receptors (i.e. TGTCT) were found widely spread (at −179, −435, −507, −903, −1392 and −1479 bp); one half site for the estrogen receptor (AGGTCA) was detected as well (at −621 bp). Although steroid receptors could potentially bind to these half palindromic sites and confer steroidal regulation of the AR gene, their actual physiological relevance is at present unclear.

Potential binding sites for certain other well-characterized transcription factors were also identified. These included Sp1 (at −50 bp and −56 bp); C/EBP (at −1197 bp); Pu.1, a DNA-binding nuclear factor of the ets oncogene protein family (at −91 bp, −402 bp, −1502 bp, and −1923 bp), the Drosophila homeobox protein Zeste (at −691 bp) and the zinc finger protein Zif 268 (at −52 bp and −60 bp). In addition, consensus motifs are located for the enhancer binding proteins PEA3 and NFκB, and for the fos/jun (AP1) heterodimer.

EXAMPLE 2

REGULATORY DOMAIN OF THE RAT ANDROGEN RECEPTOR PROMOTER

The present example is provided to demonstrate the utility of the identified regulatory domain of the androgen receptor gene between nucleotide positions −960 (position 1697 of SEQ ID NO:1) and −572 (position 2085 of SEQ ID NO:1) in regulating gene expression.

Preparation of Reporter Constructs and Expression in Cultured Cells

The initial reporter construct pAR (5.7)-Luc was produced by fusing sequences from −5.7 kb to +19 bp of the AR gene to the 5' end of the luciferase (luc) cDNA in the promoterless vector pGL2 -Enhancer (Promega, Madison, Wis.). Transcription initiation (+1 site) was established by primer extension analysis of total RNAs extracted from either the prostate or seminal vesicle. The pGL2 vector contains an SV40 enhancer and polyadenylation signal sequences at the 3' end of the luc cDNA. Utilizing specific restriction enzyme sites, several DNA constructs with shorter 5' flanking sequences were generated from the plasmid DNA pAR (5.7)-Luc. All constructs were verified by restriction enzyme mapping and DNA sequencing at the junction positions.

Bal 31 digestions produced a nested series of 5' deletion constructs. The Sma I-linearized plasmid pAR(2.4)-Luc, containing 2421 bp of the AR promoter, was digested with different concentrations (0.025–0.25 unit/μg DNA) of Bal 31 (BRL, Gaithersburg, Md.). Incubations in the presence of T4 DNA polymerase created blunt end termini of DNA fragments which were then digested with Cla I to cleave the luc cDNA at the unique site. The DNAs, with progressively shorter AR promoter sequences at the 5' end and Cla I-cleaved luc cDNA sequence at the 3' end, were ligated to the 4.4 kb Sma I/Cla I DNA fragment of the pGL2 -Enhancer vector DNA.

For transfection, cells (COS1) ($5\times10^6$) were electroporated in the presence of the luciferase DNA constructs (15 μg) and the plasmid DNA pRSV β-gal (5 μg). Cell survival after electroporation was typically 40 to 50%. Electroporated cells were seeded in T75 flasks and cultured for two days in 12 ml of DMEM-Hank's F12 (1:1) medium containing 10% fetal bovine serum. The cell extracts were assayed for luciferase and β-galactosidase activities (de Wet et al., 1987; Hall et al., 1983). Luciferase activities were normalized to constant β-galactosidase expression, and promoter strengths (as activity units) were indicated as ratios of luciferase to β-galactosidase activities.

Deletion Mutagenesis and Construction of Mutant Plasmid

PCR-based mutagenesis was used to prepare a plasmid construct, pAR (1.04,Δ960/941)-Luc, which has a 20 bp deletion at the −960/−940 position within 1047 bp of the wild-type rAR promoter. The plasmid pAR(1.04)-Luc, containing 1047 bp of the AR promoter cloned into pGL2-Enhancer, served as the PCR template for two separate reactions, one generating a 0.15 kbp and the other a 1.0 kbp DNA fragment. For the 0.15 kbp DNA, the set of PCR primers included the vector-specific GL1 primer (5' TGTATCTTATGGTACTGTAACTG 3'; SEQ ID NO:5; Promega) and the rat-AR-specific −961 antisense primer spanning positions −961 to −993 of the AR promoter. Amplification of a 1.0 kbp DNA was observed when the vector-specific GL2 primer (5' CTTTATGTTTTTG-GCGTCTTCCA 3'; SEQ ID NO:6; Promega) and the AR-specific −940 sense strand primer spanning positions −940 to −915 of the AR promoter were used for PCR. The two DNA fragments were ligated, digested with Bgl II to create the Bgl II termini and afterwards cloned at the Bgl II site of pGL2-Enhancer. The bases corresponding to positions −960 to −941 of the wild-type sequence are deleted in the mutant plasmid. This mutant plasmid was tested for AR promoter activity in transfected cells.

Results and Discussion

The following results demonstrate that an activation domain plays a dominant role in androgen receptor promoter function. A deletion mutagenesis approach was taken to examine the structure-function relationship of the AR promoter. Luciferase expression of promoter-reporter hybrid plasmids in transfected cells was assayed to determine promoter activities. The upstream 1 kb sequence was found to be sufficient for maximum promoter activity in transfected COS1 cells, since both 1.04 kb and 2.4 kb of the AR promoter showed almost equivalent promoter activities.

To identify potential regulatory domains, a nested set of exonuclease-derived 5' deletion constructs with 50 to 100 bp differences in the promoter length were examined. Luciferase expressions from various plasmid constructs are presented in FIG. 2. The 1047, 987 and 960 plasmids showed approximately similar promoter strengths. However, the activity declined by ~10-fold or more for the −940 plasmid indicating the presence of a strong activation domain upstream of the 940 position. Most surprisingly, a mutant plasmid pAR (1.04,Δ960/941)-Luc, containing 1.04 kb of the AR promoter that is internally deleted at the base positions form −960 to −941, also showed a 90% decrease in promoter activity (Table 1).

TABLE 1

AR promoter activities of wild-type
and −960/−940-deleted constructs
The plasmid pAR (1.04, Δ960/941) -Luc carries a 20 bp deletion from positions −960 to −941 within the 1.04 kbp of the AR promoter. This mutant plasmid is described in detail in above. Data represent means ± S.E.M. of three independent transfection assays.

| Promoter-reporter construct | Promoter activity Luciferase/ β-galactosidase) | (% of wild-type) |
| --- | --- | --- |
| Wild-type plasmid pAR (1.04) -Luc | 699.3 ± 49.1 | 100 |
| Mutant plasmid pAR (1.04, Δ960/941) - Luc | 67.6 ± 17 | 9.7 |

The decreased promoter function persisted in the plasmids 927, 856, 755 and 665. Partial activity was restored in the 572 plasmid, and for both 480 and 421 plasmids the levels of luciferase expression were about 90% of the maximum. The activities of these plasmids in four other cell lines, namely FTO2B (rat hepatoma), PA III (rat prostate carcinoma), L cells (mouse fibroblasts) and HeLa (human cervical carcinoma) were also examined. In all cases, a drop in promoter activity for the 940 plasmid was observed, and the extent of decline ranged from 6 to 15-fold with different cell lines (Table 2).

Figure 2:
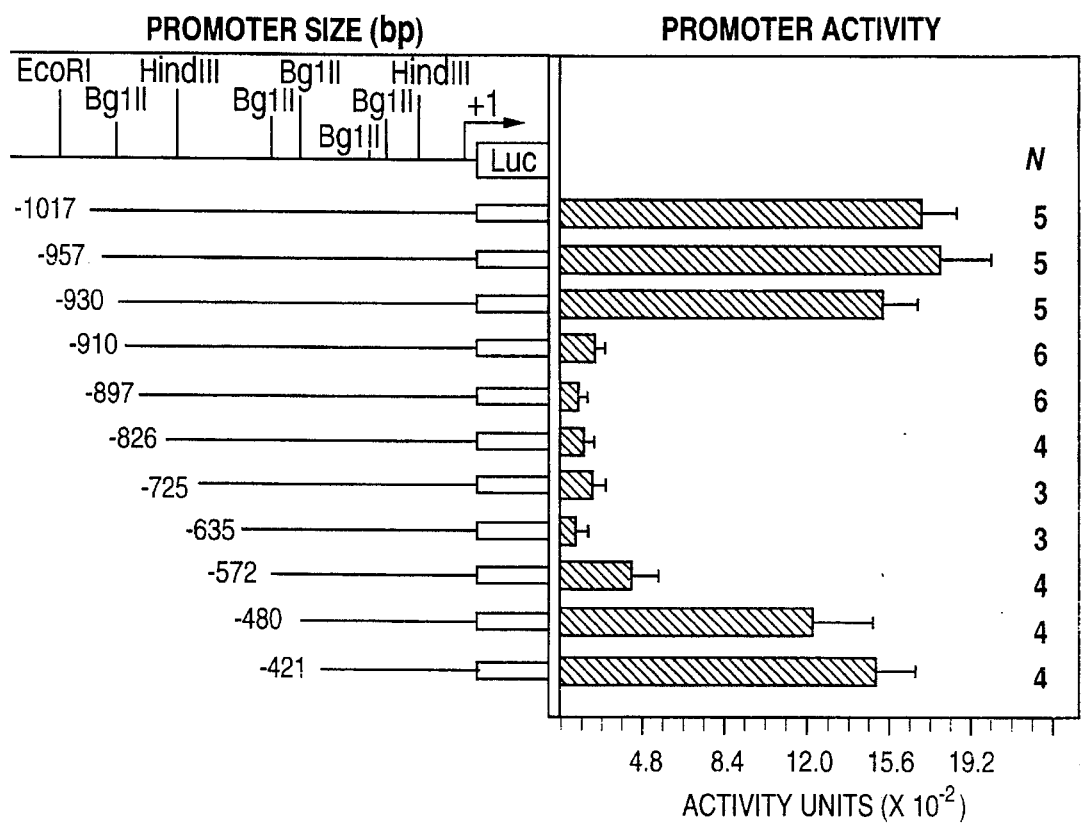
FIG. 2. Activities of progressively 5' deleted AR promoter segments as determined from luciferase expression of chimeric plasmids in transfected COS1 cells. Luciferase expression of each plasmid was normalized for the constitutive expression of β-galactosidase from the plasmid DNA pRSV β-gal. Results are the composite values of several independent transfection studies performed with three different batches of plasmid preparations. N indicates the number of individual studies carried out for each plasmid.

For all of the above analyses, luciferase activities were normalized to the constitutive expression of β-galactosidase from pRSV βgal. With such normalization, it was observed that the relative values of promoter activity for different deletion constructs remained constant. The histograms in FIG. 2 show that the AR promoter has a strong activation domain with a 5' boundary around the −960 position and a 3' boundary around the −940 position. Furthermore, a region between −480 bp and −665 bp appeared to exert a strong negative effect on the AR promoter function.

EXAMPLE 3

NUCLEAR FACTOR BINDS TO THE −960/−940 ACTIVATION DOMAIN OF AR GENE

The present example is provided to describe the nuclear factor effective in the regulation of androgen receptor gene expression of the present invention as well as to demonstrate the utility of the nuclear factor for regulating androgen receptor gene expression in vivo.

Gel Mobility Shift Analysis Methods

DNA-protein binding reactions were carried out under standard conditions (Carthew et al., 1985). Nuclear extracts from kidney and liver were prepared as described (Hattori et al., 1992). Nuclear extracts from different cell lines were prepared by established methods (Ausubel et al., 1987). Each reaction contained 30,000 cpm (~1 ng DNA) of the oligo probe and 8 µg of the nuclear extract. Protein-DNA complexes were separated on a 5% nondenaturing polyacrylamide gel, and specific radioactive bands in the dried gel were visualized through autoradiography.

Results and Discussion

The positive regulatory region of the AR promoter, as defined by transfection analysis, was examined for its ability to bind specific nuclear proteins. Whether a synthetic oligodeoxynucleotide duplex corresponding to the upstream activation domain of the rAR promoter could interact with protein(s) from a kidney nuclear extract was examined. The 965 oligo which covers positions −965 to −940 of the AR gene promoter bound to protein(s) in the kidney nuclear extract and produced a stable protein-DNA complex (FIG. 3, lane 2). Sequence specificity for this binding is indicated by the observation that the homologous oligonucleotide, but not an overlapping oligonucleotide spanning an adjacent site (−950 to −918) competed for the DNA-protein complex (FIG. 3, lanes 3 & 4).

TABLE 2

Biological activities of progressively 5'-deleted AR
promoter-reporter constructs in different cell lines
The results are means of duplicate transfection experiments

| Promoter size (bp) Cells . . . | Promoter activity (luciferase/β-galactosidase) | | | | | |
| --- | --- | --- | --- | --- | --- | --- |
| | COS 1 | FTO2B | PAIII | I-10 | L cells | HeLa |
| +19 to −987 | 501.5 | 250.5 | 29.3 | 84.9 | 24.2 | 802.5 |
| +19 to −960 | 546.0 | 285.0 | 33.1 | 123.7 | 57.4 | 971.5 |
| +19 to −940 | 44.8 | 44.0 | 5.8 | 6.8 | 11.2 | 60.0 |
| +19 to −927 | 62.9 | 62.5 | 11.5 | 4.7 | 16.3 | 118.0 |

Results of these in vitro DNA-protein binding studies suggest that nuclear protein interaction at an upstream activating sequence plays an important role in AR promoter activity. Widespread existence of this nuclear factor(s) is indicated by its detection in nuclear extracts from both rat liver and rat kidney, as well as from HeLa cells (a human cervical carcinoma cell line)(FIG. 4). Transfection assays with deletion mutants of the AR promoter in cell lines derived from mouse (L cells), rat (FTO2B, PA III), monkey (COS1) and human (HeLa) suggest that the −960/−940 region directs a critical transactivation function in all of these mammalian species and that this critical upstream region has been largely conserved throughout mammalian evolution.

The results of the present example led to the discovery of a critical upstream regulatory domain confined to a 21 bp region. In the absence of this upstream region, the promoter activity declines by more than 10-fold. The cognate nuclear factor for this upstream region appears to have a ubiquitous tissue distribution since it is detected in cell lines isolated from several different tissue types, and different animals including mouse, rat, monkey and human cells.

The above findings underscore the importance of interplay among multiple regulatory factors in the regulation of the overall expression of the AR gene in different tissues. It is anticipated that cloning and expression of cDNAs for this novel nuclear factor will be of great interest in the elucidation of transcriptional regulation of the AR gene.

EXAMPLE 4

CLONING OF THE NUCLEAR FACTOR

The present example concerns cloning the nuclear protein factor identified in Example 3. Cloning is a technique often employed by those skilled in the art to obtain a so-called "recombinant" version of a protein. Recombinant proteins may be expressed in recombinant host cells to obtain large quantities of the protein.

Cloning techniques are based upon the cloning of a DNA molecule encoding a specific protein from a DNA library, i.e., on obtaining a specific DNA molecule distinct from other portions of DNA. This can be achieved by, for example, cloning a cDNA molecule, or cloning a genomic-like DNA molecule. Techniques such as these are proposed to be of use for the production of a novel nuclear factor in accordance with the present invention.

The first step in such cloning procedures is the screening of an appropriate DNA library. In the present case, a library derived from any of the cell lines identified above may prove to be particularly suitable. The screening procedure may be an expression screening protocol employing antibodies directed against the protein, or the oligonucleotides utilized for the gel shift assays described herein. Alternatively, screening may be based on the hybridization of oligonucleotide probes, designed from a consideration of portions of the amino acid sequence of the protein, or from the DNA sequences of genes encoding related proteins. Antibodies directed against the binding protein described in Example 3 may be prepared according to techniques well known to those of skill in the art using the binding protein identified in the present disclosure as antigen.

After identifying an appropriate DNA molecule, it may be inserted into any one of the many vectors currently known in the art and transferred to a prokaryotic or eukaryotic host cell where it will direct the expression and production of the so-called recombinant version of the protein. It will be understood that although a recombinant nuclear factor may differ from the naturally-produced factor in certain ways, it will still be substantially the same protein. In particular, the degree of post-translational modifications, such as, for example, glycosylation and phosphorylation may be different between recombinant nuclear factor and that purified from a natural source such as, e.g., HeLa cells.

EXAMPLE 5

ISOLATION AND CHARACTERIZATION OF HUMAN ANDROGEN RECEPTOR (hAR) GENE PROMOTER AND IDENTIFICATION OF POSITIVE UPSTREAM ACTING REGIONS

A human genomic library will be screened with a hAR gene-specific DNA probe by standard procedures to isolate the AR gene and its 5' flanking sequence. A nested set of deletion constructs with progressive shortening of the promoter length from the 5' end with Bal 31 will be used to generate progressive deletions which will be ligated to the luciferase plasmid vector and their activities to direct luciferase gene expression will be analyzed in transfection assays.

Using these standard procedures in light of the studies presented herein, the inventor will be able to generate DNA fragments with small differences in the promoter length (within 20 to 40 bp), thus facilitating fine mapping of potential upstream regulatory regions. The upstream regions identified through deletion mutagenesis will be further authenticated by examining the promoter activities of internal deletions of the putative regulatory regions within a long promoter sequence.

EXAMPLE 6

TRIPLE HELIX FORMING OLIGONUCLEOTIDE (TFO) CORRESPONDING TO −960/−940 rAR UPSTREAM REGION

The present example is provided to demonstrate one preferred aspect of the described TFO-forming oligonucleotides of the invention. The TFO's differ from other of the oligonucleotide embodiments described herein in that they do not constitute a mirror image nucleic acid sequence of the sequence to which they bind, but instead include certain base pair substitutions (C to G, A to T) and modifications (methylation of C). These modifications enhance the stability of the triple helix by enhancing Hoogsteen bonding of TFO base pairs to DNA duplexes at a physiological pH.

The sequence of the −960/−940 region contains 81% homopurine in one of the component strands. This characteristic makes the region an excellent candidate for stable triple helix formation. Complementary TFOs generally bind with high affinity ($K_d$ $10^{-7}$ to $10^{-9}$M) to DNA duplexes at physiological pH and temperature in an antiparallel orientation relative to the purine-rich strand stabilized by Hoogsteen hydrogen bonding, generally at G.GC and T.AT triplets.

However, stable Hoogsteen bonding of the C.GC requires protonation of the single-stranded C (cytosine) that can only occur at an acidic pH. This problem with C at physiological pH can be, to a great extent, circumvented by either methylation of the C residues or substitution of G (guanine) for the C on the single strand. Substitution of T for A also allows further stabilization by formation of Hoogsteen bonding at T.AT triplets. (See FIG. 5, TFO, positions 7 and 15 are T, rather than A). It is known that substitution of a single non-bridging oxygen atom with sulfur in the phosphodiester linkage, although to some extent (about ten-fold) decreases the triplex stability, makes them highly resistant to nuclease degradation. Based on these considerations, the inventor designed and made a phosphorothioate derivative of the TFO corresponding (ODPT) to the rAR −960/−940 upstream region with the sequence structure of FIG. 5.

The TFO, 5'-GTGTTGTTGTTTGTTTTGGTGTTTTG-3' (SEQ ID NO:3), was prepared by automated DNA synthesis in a Cyclone™ DNA synthesizer.

EXAMPLE 7

INHIBITION OF ANDROGEN RECEPTOR PROMOTER ACTIVITY BY TRIPLE HELIX FORMING OLIGONUCLEOTIDES

The present example is provided to demonstrate the utility of the TFO described in Example 6 for inhibiting androgen receptor gene activity, and thus utility for the treatment of androgen-dependent pathologies, such as prostatic hypertrophy and male-pattern baldness with pharmaceutical preparations including this TFO.

The TFO as shown in FIG. 5 (SEQ ID NO:3), or a scrambled oligonucleotide (SO) of the same length and base composition was preincubated with a promoter-reporter construct containing 1.04 kb of the rAR promoter. The scramble oligo sequence is:
5'-TTTTGTTGTTGTTGTTGTGGGGTTTT-3' (SEQ ID NO:7).

Differences in luciferase activity after 20 hours of cell culture were used to compute the percent inhibition. As compared to the SO control, the specific TFO was able to cause a 60% inhibition of rAR gene promoter activity at a promoter:TFO ratio of 1:550 (FIG. 6).

These results demonstrate the utility of the described TFOs as non-toxic and highly specific anti-androgenic agents that may be used for the management of prostatic hyperplasia and male pattern baldness. In addition, various chemical modifications of the TFO corresponding to the rAR upstream region may be prepared using the present disclosure of the sequence and location of the critical androgen receptor gene promoter region to even further enhance biological effect (i.e., decreased AR gene activity) at the lowest possible nucleotide amounts and concentrations. Antigene TFO drugs may also be developed given the present disclosure of the AR gene promoter region and routine further cloning and characterization of the human AR gene promoter.

EXAMPLE 8

TRANSFECTION ASSAY OF THE PROMOTER-REPORTER CONSTRUCT AND THE EFFECT OF THE ANTISENSE OLIGONUCLEOTIDE

The present example demonstrates the utility of the presently described oligonucleotides for the inhibition of AR gene expression in the intact cell (in cellulo). In addition, the utility of the invention for treating androgen receptor gene-dependent pathologies is also established.

Methods

For transfection, cells (5×10$^6$) were electroporated in the presence of 15 µg luciferase DNA construct (1.1 kilobase androgen receptor promoter ligated to the firefly luciferase reporter gene). Plasmid DNAs were purified through the Qiagen anion exchange resin (Qiagen, Chatsworth, Calif.). Cells were electroporated at 960 µF and 320 V, followed by culture in 12 ml of the DMEM-Hank's F12 (1:1) medium containing 10% fetal bovine serum. Cell survival after electroporation was typically 40 to 50%.

Electroporated cells were seeded in T75 flasks and cultured for five hours before the addition of the single-stranded oligodeoxyphosphorothioate (ODPT). A 26-nucleotide long ODPT spanning −965 to −940 positions of the rat androgen receptor gene at either the sense or antisense orientation was used. A scrambled ODPT containing the same AT/GC ratio was used as a control. Cells were harvested 48 hrs after electroporation, cell extracts were prepared, and assayed for luciferase activities according to de Wet et al. (1987). The luciferase activities were measured in a Bio-Orbit luminometer (Pharmacia-LKB, Gaithersburg, Md.) and the values were normalized for the amount of total cellular protein.

Results

In these studies, either the TFO shown in FIG. 5 or a scrambled oligonucleotide (SO) of the same length and base composition was added to cells that had been electroporated with a promoter-reporter construct containing 1.04 kb of the rAR promoter. As compared to the SO control, the specific TFO was able to cause a 60% inhibition of the rAR gene promoter activity at a promoter:TFO ratio of 1:550 (FIG. 6).

EXAMPLE 9

STRUCTURAL MODIFICATIONS OF RAT AND HUMAN TFOs TO OPTIMIZE INHIBITORY ACTIVITY

The present inventor proposes to examine various chemical modifications of the triple helix forming oligonucleotide (TFO) for the development of a more sensitive and biologically stable anti-AR TFO. The antigene effect of the TFO can be enhanced by increasing cellular uptake, decreasing degradation and stabilizing the triple helix. Since improvement in the first two parameters may be detrimental to the stability of the triple helix, optimization of these conditions for maximizing the biological effect will be the ultimate goal.

The sequence complementary to the purine-rich strand of the −960/−940 rAR region contains five C bases and in preliminary studies, the inventor has replaced them with G. Recently, Jetter and Hobbs have shown that replacement of the cytosines with 8-oxoadenines on the third strand greatly enhances the stability of the triplex at the physiological pH (Jetter, M. C., and Hobbs F. W. (1993), Biochemistry 32:3249–3254). It is envisioned that the rAR −960/−940 upstream region TFO with 8-oxoA will be assayed in the inventor's transfection system. The 8-oxoA substituted TFO will be tested both as natural oligonucleotides and as a phosphorothioate containing analog. The TFO and the scrambled oligonucleotide will be transfected into COS1 cells with and without prior preincubation with the rAR promoter-reported construct. The gene-specific effect of the TFO will be further authenticated by cotransfection with a different promoter-reporter construct, e.g., RSVβ-gal and TKβ-gal. The in vitro stabilization of the triplex after such modifications will be examined through band shift and footprinting analyses.

Thuong and Chassignal have shown that attachment of acridine orange, an intercalating agent, to the 5'-end of the TFO greatly enhances the stability of the triple helix (Thuong, N. T., Chassignol, M. (1988), Tetrahedron Letts. 29:5905–5908). This type of conjugated TFO can be synthesized by automated solid-phase DNA synthesis where the acridine moiety is introduced via an acridine-phosphoramidite. The inventor will test the acridine conjugated anti rAR −960/−940 TFO for both enhanced stability through bandshift assay at different TFO to duplex ratios, and on its inhibitory effect on the promoter function in the transfection system.

Attachment of a cholesterol moiety to either the 3' or the 5' end of the TFO is known to markedly enhance its cellular uptake. It is contemplated that such a TFO conjugate containing cholesterol will be biologically effective and will be of great value in the development of a hair cream that can potentially inhibit the AR gene expression within the hair follicles. This can be further improved in conjunction with increased skin circulation by minoxidil.

As indicated by the rat data, a strong upstream activating region with homopurine/homopyrimidine domain may also play a critical role in the regulation of the human androgen receptor (hAR) gene promoter. Thus, based on the information derived from the sequence modification of the TFO complementary to the rAR −960/−940 region, and the standardized transfection condition, the inventors will be able to develop the appropriate TFO for the hAR.

Once both the rAR and hAR antigene TFOs are obtained, the in vivo effectiveness and toxicity studies may be conducted. For these studies the homologous rat system may provide a more suitable pharmacological/toxicological model where not only the systemic toxicity but also the suppression of the rat AR gene expression in target tissues such as the prostate, can be conveniently monitored.

EXAMPLE 10

METHOD FOR PREPARING TOPICAL PREPARATION OF TRIPLE HELIX FORMING OLIGONUCLEOTIDES

The present example demonstrates one proposed method whereby the described oligonucleotides, particularly the TFO oligonucleotide 5'-GTGTTGTTGTTTGTTTTGGT-GTTTTG-3' (SEQ ID NO:3)(26 bp), may be formulated into an effective pharmacological preparation in a pharmaceutically acceptable carrier.

In a most preferred embodiment, a cholesterol moiety will be attached at the 3' end of the TFO. This modification is expected to markedly enhance cellular uptake and nuclear localization of the TFO. Cholesterol modified oligonucleotides may be synthesized with a cholesterol phosphoramidite reagent on an automatic oligonucleotide synthesizer.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is contemplated that such a TFO conjugate containing cholesterol will be biologically effective and will be of great value in the development of a hair cream that can potentially inhibit the AR gene expression within the cells of the hair follicles. Typically, such compositions are prepared either as liquid solutions or suspensions; solid forms suitable for solution in, or suspension in, liquid prior to injection can also be prepared. The preparation can also be emulsified.

EXAMPLE 11

METHOD FOR PREPARING OLIGONUCLEOTIDES TO THE −100 TO −150 REGION OF THE ANDROGEN RECEPTOR GENE

The present example is provided to demonstrate one method whereby oligonucleotides corresponding to the −150 to −100 nucleotide region of the androgen receptor gene may be prepared. The −150 to −100 region of the androgen receptor gene contains polypurine/polypyrimidine stretch and is conserved both in the rat and human. The present appears to be important, if not critical, to expression of the androgen receptor gene. This is because this region of the androgen receptor gene is pyrimidine rich, and the present inventors have demonstrated that the pyrimidine-rich region at the −960 to −940 nucleotides of the androgen receptor gene promoter greatly affects the level of androgen receptor gene transcription.

The nucleotide sequence of the androgen receptor gene between nucleotides −150 to −100 is:

5'-GCGGTGAGGGGAGGGGAGAAAAGGAAAGGGGAGGGGAGGGGAGGGGAGGGGA-3'
(position 2506 to 1556 of SEQ ID NO:1.)

Upon formulation, solutions will be administered in a manner compatible with the dosage formulation and in such amount as is therapeutically effective. The formulations are easily administered in a variety of dosage forms such as injectable solutions, drug release capsules and the like.

A complementary oligonucleotide to this segment of the androgen receptor gene will be prepared using standard oligonucleotide synthesis techniques. By way of example, a specific method by which the present inventors propose to synthesize this oligonucleotide is by the same procedure as described under Example 7.

Upon synthesis of the oligonucleotide, inhibition studies may be conducted to determine the degree of androgen receptor gene inhibition in cellulo. In a related embodiment, the oligonucleotide complementary to this region of the androgen receptor gene may be prepared wherein the "C" nucleotides are replaced by "G" nucleotides. This is expected to enhance the stability of the formed triple helix.

Increasingly smaller fragments of the 50-base pair oligonucleotide at the region may be examined in cellulo to determine percent inhibition. These studies will more closely identify those regions of the androgen receptor gene promoter necessary for androgen receptor gene expression.

The oligonucleotide directed to this segment of the androgen receptor gene may also be modified so as to include methyl groups at the "C" bases. This modification is expected to enhance the stability of the oligonucleotide in cellulo.

EXAMPLE 12

METHYLATED OLIGONUCLEOTIDES AND TRIPLE HELIX FORMING OLIGONUCLEOTIDES

The present example is provided to demonstrate one method by which the various oligonucleotides of the present invention may be methylated at particular base pair sites to enhance stability of the molecule in cellulo. It is expected that methylation of the oligonucleotides directed to the various segments of the androgen receptor gene, specifically at "C" will not impair the inhibitory activity as these oligonucleotides on androgen receptor gene expression, and will provide the added advantage of enhancing the stability of the molecule in vivo.

According to one proposed method, the following oligonucleotide sequences may be methylated at the "C" residues.

| Sequence | Position/ID |
|---|---|
| 5'-GATCTTTCTATTGCTCTTTTG-3' | position 1697 to 1717 of SEQ ID NO:1 |
| 3'-CTAGAAAGATAACGAGAAAAC-5' | SEQ ID NO:2 |
| 5'-GTTGTTTGTTTTGGTGTTTTG-3' | position 6 to 25 of SEQ ID NO:3 |
| 3'-GATCTTTCTATTGCTCTTTTG-5' | SEQ ID NO:8 |

Methylation nucleotides will be introduced in appropriate positions of the oligonucleotide sequence during automated synthesis cycles.

EXAMPLE 13

METHOD FOR PREVENTING HAIR LOSS IN A TREATMENT FOR HUMAN MALE PATTERN BALDNESS

The present example is provided to demonstrate a method by which the preparations of the present invention may be used in the treatment of human androgen dependent hair loss, particularly the hair loss characteristic in male-pattern baldness.

The TFO formulations, particularly those modified to include a cholesterol moiety, may be added to hair creams and other cream or salve-like carriers suitable for application to the hair follicles of the scalp. While the preparations may be used alone, it is anticipated that other agents may be added to the preparation to enhance circulation. By way of example, an agent that enhances circulation is minoxidil.

Amounts of the oligonucleotide within an ointment or cream for topical application that are thought to be useful for treatment of male pattern baldness applied to the scalp are between about 0.01 mg/ml and about 0.1 mg/ml. Most preferably, the range of ingredient oligonucleotide to be included in a topical preparation is between about 0.01 mg/ml and about 0.05 mg/ml. Topical preparations that include at least 0.01 mg/ml of the stabilized oligonucleotide in a cream or ointment preparation are anticipated to provide a sufficient amount of the active ingredient oligonucleotide/ TFO to the hair follicle cells of, for example, the scalp, sufficient to enter these cells and decrease androgen gene expression.

Because over-action of androgen is known to be characteristic of patients with male-pattern baldness, the described preparations may provide a treatment for this condition by effectively decreasing androgen receptor gene expression in these tissues.

According to one embodiment of the method the oligonucleotide with the cholesterol moiety attached to the 5' end at a concentration of 0.1 mg/ml added to the lanolin and oil-based hair cream will be applied to the scalp daily to prevent the hair loss.

EXAMPLE 14

PROPOSED METHOD FOR TREATMENT OF PROSTATIC HYPERTROPHY

In conjunction with other already available medications such as Proscar®, systemic administration of the antigene AR oligo will provide an additional measure to reduce prostatic hypertrophy.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

EXAMPLE 15

USE OF OLIGONUCLEOTIDES IN HYBRIDIZATION

In addition to their use in directing the expression of the AR protein, the nucleic acid sequences disclosed herein also have a variety of other uses. For example, they also have utility as probes or primers in nucleic acid hybridization embodiments. As such, it is contemplated that oligonucleotide fragments corresponding to the sequence of SEQ ID NO:1 for stretches of between about 10 to 15 nucleotides and about 20 to 30 nucleotides will find particular utility. Longer complementary sequences, e.g., those of about 40, 50, 100, 200, 500, 1000, and even up to full length sequences of about 2775 nucleotides in length, will also be of use in certain embodiments.

The ability of such nucleic acid probes to specifically hybridize to AR promoter sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having stretches of 10, 20, 30, 50, or even of 100 nucleotides or so, complementary to SEQ ID NO:1, is particularly contemplated as hybridization probes for use in, e.g., Southern and Northern blotting. This would allow the structural analysis of regulatory genes to be analysed, both in model systems, e.g. transfection of COS-1 cells, diverse cell types and also in various patients or in other mammalian cells. The total size of fragment, as well as the size of the complementary stretch(es), will ultimately depend on the intended use or application of the particular nucleic acid segment. Smaller fragments will generally find use in hybridization embodiments, wherein the length of the complementary region may be varied, such as between about 10 and about 100 nucleotides, but larger complementarity stretches of up to about 2500 nucleotides may be used, according to the length complementary sequences one wishes to detect.

The use of a hybridization probe of about 10 nucleotides in length allows the formation of a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired.

Hybridization probes may be selected from any portion of any of the sequences disclosed herein. All that is required is to review the sequence set forth in SEQ ID NO:1 and to select any continuous portion of the sequence, from about 10 nucleotides in length up to and including the full length sequence, that one wishes to utilize as a probe or primer. The choice of probe and primer sequences may be governed by various factors, such as, by way of example only, one may which to employ primers from towards the termini of the total sequence, or from the ends of the functional domain-encoding sequences, in order to amplify further DNA; one may employ probes corresponding to the entire DNA, or to the upstream promoter region, to clone related genes from other species or to clone other promoters with similar regulatory regions or homologous genes from any species including human; and one may employ wild-type and mutant probes or primers with sequences centered around the relevant transcriptional activation regions to screen DNA samples for genetic polymorphisms, such as to identify human subjects which carry the genetic variation responsible for disease conditions related to expression of the androgen receptor.

The process of selecting and preparing a nucleic acid segment which includes a sequence from within SEQ ID NO:1 may alternatively be described as preparing a nucleic acid fragment. Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR technology of U.S. Pat. No. 4,603,102 (incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of related or homologous gene regions. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by 0.02M–0.15M NaCl at temperatures of 50° C. to 70° C. Such selective conditions tolerate little, if any, mismatch between the probe and the template or target strand, and would be particularly suitable for isolating highly related promoter regions.

Of course, for some applications, for example, where one desires to prepare mutants employing a mutant primer strand hybridized to an underlying template or where one seeks to isolate promoter regions from related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to SEQ ID NO:1, such as about 10 nucleotides, and which are up to 10,000 or 5,000 base pairs in length, with segments of 3,000 being preferred in certain cases. DNA segments with total lengths of about 1,000, 500, 200, 100 and about 50 base pairs in length are also contemplated to be useful.

It will also be understood that this invention is not limited to the particular nucleic acid sequences of SEQ ID NO:1–9. Recombinant vectors and isolated DNA segments may therefore variously include the non-coding regions themselves, coding regions bearing selected alterations or modifications in the basic coding region, or they may encode larger polypeptides which nevertheless include non-coding regions or may encode biologically functional equivalent proteins or peptides which have variant amino acids sequences.

The DNA segments of the present invention encompass biologically functional equivalent promoters. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the activity of the promoter or to test deletion or chimeric mutants in order to examine promoter activity at the molecular level.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All claimed matter and methods can be made and executed without undue experimentation.

The following references, to the extent that they provide exemplary procedural or other details supplementary to those set forth herein, are specifically incorporated herein by reference.

Ausubel et al., (1987) Curr. Prot. Mol. Biol., John Wiley & Sons, New York.

Baarends et al., (1990) Mol. Cell. Endocrinol., 74:75–84.

Bankier et al., (1987) Meth. Enzymol. 155:51–93.

Beato M. (1989), Cell, 56:335–344.

Biggin M. D., and Tjian, R. (1989) Trends in Gent., 5:377–383.

Briggs et al. (1986) Science, 234:47–52.

Carthew et al., (1985) Cell, 43:439–448.

Chang et al., (1988) Science, 240:324–326.

Christy, B., and Nathans, D. (1989) Proc. Natl. Acad. Sci. USA 86:8737–8741.

Coffey et al., (1987) Prog. Clin. Biol. Res. 239:1–73.

Colvard et al., (1989) Proc. Natl. Acad. Sci. USA 86:854–857.

Curran, T., and Franza, B. R. (1988) Cell 55:395–397.

deWet et al., (1987) Mol. Cell Biol. 2:1044–1051, Firefly Luciferase Gene: Structure and Expression in Mammalian Cells.

Encio, I. J., and Detera-Wadleigh, S. D. (1992) J. Biol. Chem., 266:7182–7188.

Evans, R. M. (1988) Science, 240:889–895.

Faber et al., (1992) J. Biol. Chem., 266:10743–10749.

Hall et al., (1983) J. Mol. Appl. Genet., 2:101–105.

Harris et al., (1992) Proc. Natl. Acad. Sci. USA, 89:10787–10791, Identification and Selective Inhibition of an Isoenzyme of Steroid 5α-Reductase in Human Scalp.

Hattori et al., (1992) DNA Cell Biol., 10:777–781.

Huckaby et al., (1987) Proc. Natl. Acad. Sci. USA, 84:8380–8384.

Isseman, I., and Green, S. (1990) Nature 347, 645–650.

Jenster et al., (1992) J. Steroid Biochem. Mol. Biol., 41:671–675.

Klemsz et al., (1990) Cell 61:113–124.

Kreig et al. (1993) Proc. Natl. Acad. Sci. USA, 90, 1045–1052.

Leclerc et al., (1992) J. Biol. Chem., 266:8711–8719.

Lubahn et al., (1988) Science, 240:327–330.

Marcelli et al. (1992) J. Clin. Endocrinol. Metab., 73(2):318–325

Martin et al., (1988) Proc. Natl. Acad. Sci. USA, 85:5839–5843.

McEwen, B. S. (1980) Ann. Rev. Phys. 42:97–110.

Milin, B., and Roy, A. K. (1973) Nature New Biol. 242, 248–250.

Newmark et al., (1992) Proc. natl. Acad. Sci. USA 89:6319–6323.

O'Malley, B. W. (1990) Mol. Endocrinol. 4:363–369.

Pajunen et al., (1982) J. Biol. Chem. 257:8190–8198.

Pinsky, L., and Kaufman, M. (1987) Adv. Hum. Genet., 16:299–472.

Prestridge, D. S. (1992) CABIOS, 7:203–206.

Ron et al., (1990) Mol. Cell Biol., 10:1023–1032.

Saunders et al. (1992) Clin. Endocrin., 37(3):

Song et al., (1991) Endocrinol., 128:349–356.

Stoner, E., (1990) J. Steroid Biochem. Molec. Biol., 37(3):375–378.

Tilley et al., (1990) J. Biol. Chem., 265:13776–13781.

Trapman et al. (1988) Biochem. Biophys. Res. Commun. (USA), 153(1):241–248.

Vinson et al., (1989) Science, 246:911–916.

Yarbrough et al., (1990) J. Biol. Chem., 265:8893–9800.

---

What is claimed is:

1. An oligonucleotide comprising a nucleic acid sequence of a distal activation promoter region upstream of nucleotide position −570 of the sequence at FIG. 1, said position corresponding to position 2087 of SEQ ID NO:1.

2. The oligonucleotide of claim 1 comprising a nucleic acid sequence as defined by position 1697 to 2087 of SEQ ID NO:1.

3. The oligonucleotide of claim 1, comprising a nucleic acid sequence defined by position 1697 to 1992 of SEQ ID NO:1.

4. The oligonucleotide of claim 1, comprising a nucleic acid sequence as defined by position 1697 to 1902 of SEQ ID NO:1.

5. The oligonucleotide of claim 1, comprising a nucleic acid sequence as defined by position 1697 to 1801 of SEQ ID NO:1.

6. The oligonucleotide of claim 1, comprising a nucleic acid sequence as defined by position 1967 to 1730 of SEQ ID NO:1.

7. The oligonucleotide of claim 1, comprising a nucleic acid sequence as defined by position 1697 to 1717 of SEQ ID NO:1.

8. The oligonucleotide of claim 1, comprising a nucleic acid sequence as defined by position 1692 to 1717 of SEQ ID NO:1.

9. The oligonucleotide of claim 1, wherein at least one cytosine of the sequence is methylated.

10. The oligonucleotide of claim 1, wherein at least one guanine of the sequence is methylated.

11. The oligonucleotide of claim 9, wherein at least one of the guanine nucleotides is methylated.

12. The oligonucleotide of claim 1, further comprising a cholesterol moiety.

13. The oligonucleotide of claim 12, wherein a cholesterol moiety is attached to a terminal nucleotide.

14. The oligonucleotide of claim 13, wherein a cholesterol moiety is attached to each terminal nucleotide.

15. The oligonucleotide of claim 1, further defined as a deoxyoligonucleotide.

* * * * *